(12) United States Patent
Diwu et al.

(10) Patent No.: US 8,329,390 B2
(45) Date of Patent: Dec. 11, 2012

(54) DETECTION OF TRANSMEMBRANE POTENTIALS USING N,N,N'-TRIALKYL THIOBARBITURIC ACID-DERIVED POLYMETHINE OXONOLS

(75) Inventors: Zhenjun Diwu, Sunnyvale, CA (US); Jianjun He, Sunnyvale, CA (US); Yi Tang, Sunnyvale, CA (US)

(73) Assignee: AnaSpec Incorporated, Fremont, CA (US)

( * ) Notice: Subject to any disclaimer, the term of this patent is extended or adjusted under 35 U.S.C. 154(b) by 0 days.

(21) Appl. No.: 11/212,203

(22) Filed: Aug. 25, 2005

(65) Prior Publication Data
US 2006/0088816 A1 Apr. 27, 2006

Related U.S. Application Data

(63) Continuation-in-part of application No. 10/971,311, filed on Oct. 21, 2004, now abandoned.

(51) Int. Cl.
*C12Q 1/00* (2006.01)
*C07D 403/00* (2006.01)
*C07D 239/10* (2006.01)
*C07D 239/66* (2006.01)

(52) U.S. Cl. .............................. 435/4; 544/296; 544/298
(58) Field of Classification Search .................. None
See application file for complete search history.

(56) References Cited

U.S. PATENT DOCUMENTS

| 4,560,665 | A | 12/1985 | Nakae et al. |
| 4,861,727 | A | 8/1989 | Hauenstein et al. |
| 4,900,934 | A | 2/1990 | Peeters et al. |
| 5,244,813 | A | 9/1993 | Walt et al. |
| 5,661,035 | A | 8/1997 | Tsien et al. |
| 6,107,066 | A | 8/2000 | Tsien et al. |
| 2003/0087332 | A1 | 5/2003 | Klaubert et al. |
| 2003/0100059 | A1 | 5/2003 | Yao et al. |

FOREIGN PATENT DOCUMENTS

| EP | 137515 | 10/1984 |
| EP | 397641 | 4/1990 |
| EP | 429907 | 11/1990 |
| EP | 520262 | 6/1992 |
| EP | 552107 | 1/1993 |
| WO | WO 9508637 | 3/1995 |
| WO | WO 9527204 | 10/1995 |
| WO | WO 96/41166 | * 12/1996 |
| WO | WO 98/30715 | 7/1998 |
| WO | WO 03/014701 | * 2/2003 |

OTHER PUBLICATIONS

Burgstahler, R. et al., "Confocal ratiometric voltage imaging of cultured human keratinocytes reveals . . . " Am J Physiol Cell Physiol 284, C944-52 (2003).
Coclet-Nimin, J. et al., "Discrimination between cystic fibrosis and CFTR-corrected epithelial cells by a membrane potential-sensitive . . . " Exp Lung Res 28, 181-199 (2002).
Baxter, D.F., et al., "A novel membrane potential-sensitive flourescent dye improves cell-based assays for ion channels," J Biomol Screen 7, 79 (2002).
Falconer, M., et al., "High-throughput screening for ion channel modulators" J Biomol Screen 7, 460 (2002).
Adkins, C.E., et al., "alpha4beta3delta GABA(A) receptors characterized by fluorescence resonance energy transfer-derived measurements of . . . " J Biol Chem 276, 38934-9 (2001).
Suh, B.C., et al., "P2x(7) nucleotide receptor mediation of membrane pore formation and superoxide generation in humanpromyelocytes . . . " J Immunol 166, 6754-6763 (2001).
Cacciator, T.W., et al., "Identification of neurol circuits by imaging coherent electrical activity with FRET-based dyes," Neuron 23, 449-459 (1999).
Gonzales, J.E., Tsien, R.Y., "Improved indicators of cell membrane potential that use fluorescence resonance energy transfer," Chem Biol 4, 269-277 (1997).
Dall'Asta, V., et al., "Membrane potential changes visualized in complete growth media through confocal laser scanning microscopy," Exp Cell Res 231, 260-268 (1997).
Marriott, I., & Mason, M.J., "Evidence for a phorbol ester-insensitive phosphorylation step in capacitative calcium entry in rat thymic . . . ," J Biol Chem 271, 26732-26738.

(Continued)

*Primary Examiner* — Ernst Arnold
(74) *Attorney, Agent, or Firm* — McKinney Law Group; Jeffrey A. McKinney

(57) ABSTRACT

The present invention relates generally to the detection and measurement of transmembrane potentials using an N,N,N'-trialkyl thiobarbituric acid-derived polymethine oxonol (shown below). In particular, the present invention is directed to compositions and optical methods for determining transmembrane potentials across the plasma membrane of biological cells using a slightly hydrophobic N,N,N'-trialkyl thiobarbituric acid-derived polymethine oxonols. The method comprises a slightly hydrophobic N,N,N'-trialkyl thiobarbituric acid-derived polymethine oxonol anion capable of redistributing from a first face of the membrane to a second face of the membrane in response to changes in the potential of the membrane. In one aspect the method is used to identify compounds which modulate membrane potentials in biological membranes.

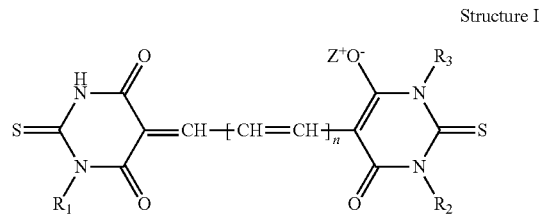

Structure I wherein R1, R2, and R3 are independently selected from the group consisting of hydrogen, alkyl, haloalkyl and heteroalkyl; n is an integer from 1 to 3; Z is Na, K, ammonium or other biologically acceptable salt.

4 Claims, 12 Drawing Sheets

OTHER PUBLICATIONS

Rader, R.K., et al., "T cell activation is regulated by voltage-dependent and calcium-activated potassium channels," J Immunol 156, 1425-1430 (1996).

Ferrari, D., et al., "Mouse microglial cells express a plasma membrane pore gated by extracellular ATP," J Immunol 156, 1531-1539 (1996).

Plasek, J., & Sigler, K., "Slow fluorescent indicators of membrane potential: a survey of different approaches to probe response . . . " J Photochem Photobiol B 33, 101-124 (1996).

Amoroso, S., et al., "The A1 agonist CCPA reduced bisoxonol-monitored membrane potential depolarization elicited by high K+ in . . . " Biochim Biophys Acta 1239, 67-73 (1995).

Verkman, A.S., "Optical methods to measure membrane transport processes," J Membr Biol 148, 99-110 (1995).

Loew, L.W., "Characterization of Potentiometric Membrane Dyes," Adv Chem Ser 235, 151 (1994).

Kim, W.K. & Rabin, R.A., "Characterization of the purinergic P2 receptors in PC12 cells. Evidence for a novel subtype," J Biol Chem 269, 6471-6477 (1994).

Dall'Asta, V., et al., "Response of human fibroblasts to hypertonic stress. Cell shrinkage is counteracted by an enhanced . . . " J Biol Chem 269, 10485-10491 (1994).

Cabado, A.G., "Effect of ion composition on the changes in membrane potential induced with several stimuli in rat mast cells," J Cell Physiol 158, 309-316 (1994).

Shapiro H.M., "Cell membrane potential analysis," Methods Cell Biol 41, 121-133 (1994).

Tanner, M.K., et al., "Flow cytometric analysis of altered mononuclear cell transmembrane potential induced by cyclosporin," Cytometry 14, 59-69 (1993).

Lukacs, G.L., et al., "The delta F508 mutation decreases the stabilty of cystic fibrosis transmembrane conductance regulator in the . . . ," J Biol Chem 268, 21592-21598 (1993).

Schwartz, M.A., "Spreading of human endothelial cells onfibronectin or vitronectin triggers elevation of intracellular free calcium," J Cell Biol 120, 1003-1010 (1993).

Loew, L.M., "Confocal microscopy of potentiometric fluorescent dyes," Methods Cell Biol 38, 195-209 (1993).

Seamer, L.C., & Mandler, R.N., "Method to improve the sensitivity of flow cytometric membrane potential measurements in mouse spinal . . . ," Cytometry 13, 545-552 (1992).

Bronner, C., & Landry, Y., "The use of the potential-sensitive fluorescent probe bisoxonol in mast cells," Biochim Biophys Acta 1070, 321-331 (1991) (abstract only).

Taglialatela, M., et al., "Effect of maitotoxin on cytosolic Ca2+ levels and membrane potential in purified rat brain," Biochim Biophys Acta 1026, 126-132 (1990).

Pittet, D., et al, "Correlation between plasma membrane potential and second messenger generation in the promyelocytic cell line HL-60," J Biol Chem 265, 14256-14263 (1990).

Freedman, J.C., & Novak, T.S., "Optical measurement of membrane potential in cells, organelles, and vesicles," Methods Enzymol 172, 102-122 (1989).

Sahlin, S., et al., "Differentiation between attached and ingested immune complexes by a fluorescence quenching cytofluorometric assay," J. Immunol Methods 60, 115-124 (1983).

* cited by examiner

DETECTION OF TRANSMEMBRANE POTENTIALS USING N,N,N'-TRIALKYL THIOBARBITURIC ACID-DERIVED POLYMETHINE OXONOLS

CROSS-REFERENCE TO RELATED APPLICATION

This application claims priority as a continuation in part to U.S. patent application Ser. No. 10/971,311, filed Oct. 21, 2004, now abandoned the entire disclosure of which is incorporated by reference.

STATEMENT REGARDING FEDERALLY SPONSORED RESEARCH OR DEVELOPMENT

This invention was made with United States government support awarded by National Institute of Health NIH grant 2R44NS44641. The United States has certain rights in this invention.

BACKGROUND OF THE INVENTION

1. Field of the Invention

The present invention relates generally to the detection and measurement of transmembrane potentials using an N,N,N'-trialkyl thiobarbituric acid-derived polymethine oxonol. In particular, the present invention is directed to compositions and optical methods for determining transmembrane potentials across the plasma membrane of biological cells using a slightly hydrophobic N,N,N'-trialkyl thiobarbituric acid-derived polymethine oxonols. The method comprises a slightly hydrophobic N,N,N'-trialkyl thiobarbituric acid-derived polymethine oxonol anion capable of redistributing from a first face of the membrane to a second face of the membrane in response to changes in the potential of the membrane. In one aspect the method is used to identify compounds which modulate membrane potentials in biological membranes.

2. Background of the Art

The plasma membrane of a cell typically has a transmembrane potential of approximately −70 mV (negative inside) as a consequence of $K^+$, $Na^+$ and $Cl^-$ concentration gradients that are maintained by active transport processes. Increases and decreases in membrane potential (referred to as membrane hyperpolarization and depolarization, respectively) play a central role in many physiological processes, including nerve-impulse propagation, muscle contraction, cell signaling and ion-channel gating [Shapiro H M. "Cell membrane potential analysis." *Methods Cell Biol* 41, 121-133 (1994); Baxter D F, Kirk M, Garcia A F, Raimondi A, Holmqvist M H, Flint K K, Bojanic D, Distefano P S, Curtis R, Xie Y. "A novel membrane potential-sensitive fluorescent dye improves cell-based assays for ion channels." *J Biomol Screen* 7, 79 (2002); Falconer M, Smith F, Surah-Narwal S, Congrave G, Liu Z, Hayater P, Ciaramella G, Keighley W, Haddock P, Waldron G, Sewing A. "High-throughput screening for ion channel modulators" *J Biomol Screen* 7, 460 (2002)]. In general, there are two distinct methods to measure cell membranes, (a) direct electrical measurement of cell membrane potentials, e.g, the so-called 'Patch Clamping' technique, and (b) indirect optical sensing of membrane potentials using a membrane potential-sensitive dye as an indicator. Fluorescence detection and imaging of cellular electrical activity is a technique of great importance [Grinvald, A., Frostig, R. D., Lieke, E., and Hildesheim, R. "Optical imaging of neuronal activity." *Physiol. Rev.* 68, 1285-1366 (1988); Salzberg, B. M. "Optical recording of electrical activity in neurons using molecular probes." In *Current Methods in Cellular Neurobiology*. J. L. Barker (editor) Wiley, New York. 1983, pp 139-187; Cohen, L. B. and S. Lesher. "Optical monitoring of membrane potential: methods of multisite optical measurement." In *Optical Methods in Cell Physiology*. P. de Weer and B. M. Salzberg (editors), 1985, Wiley, New York. pp 71-99]. The optical method that uses a fluorescent indicator has steadily gained popularity in recent years due to its convenience, high throughput and improved sensitivity. Potentiometric probes are a critical factor in the optical measurement of membrane potentials. The existing potentiometric probes include the cationic or zwitterionic styryl dyes, the cationic carbocyanines and rhodamines, the anionic oxonols and hybrid oxonols and merocyanine 540. The class of dyes determines factors such as accumulation in cells, response mechanism and toxicity. The fluorescent indicators used in the optical measurement of membrane potential have been traditionally divided into two classes:

(1) Fast-Response Dyes:

These dyes are usually cell-impermeable and have fast response to changes in membrane potentials because they need little or no translocation. [Loew, L. M., "How to choose a potentiometric membrane probe", In *Spectroscopic Membrane Probes*. CRC Press, Boca Raton L., 1988, pp 139-151; Loew, L. M., "Potentiometric membrane dyes", In *Fluorescent and Luminescent Probes for Biological Activity*. W. T. Mason (editor), Academic Press, San Diego, 1993, pp 150-160]. However, they are insensitive because they sense the electric field with only a part of a unit charge moving less than the length of the molecule, which in turn is only a small fraction of the distance across the membrane. Furthermore, a significant fraction of the total dye signal comes from molecules that sit on irrelevant membranes or cells and that dilute the signal from the few correctly placed molecules.

(2) Slow-Response Dyes:

In contrast to the above-mentioned 'fast-response' dyes, these dyes are usually hydrophobic and cell-permeable. They are quite sensitive although they have a slow redistribution of permeant ionized dyes from the extracellular medium into the cell. The ratio of their concentrations between the inside and outside of the cell can change by up to the Nernstian limit of 10 fold for a 60 mV change in transmembrane potential. However, for the permeable ions to establish new equilibria, the dye ions must diffuse through unstirred layers in each aqueous phase and the low-dielectric-constant interior of the plasma membrane. These processes result in their slow responses to changes in membrane potentials. Moreover, such dyes distribute into all available hydrophobic binding sites indiscriminately. Therefore, selectivity between cell types is difficult. Additionally, any additions of hydrophobic proteins or reagents to the external solution, or changes in exposure to hydrophobic surfaces, are prone to cause artifacts.

In view of the above drawbacks of existing fluorescent dyes used in optical measurement of membrane potentials, improved methods and compositions are needed to detect small variations in transmembrane potentials with a rapid response and strong fluorescence signal, preferably on a millisecond to second timescale. Also urgently needed are methods and compositions less susceptible to the effects of changes in external solution composition, in particular, eliminating the serum effect. The critical factors to develop such membrane potential detection technologies are the effective design and synthesis and testing/screening of membrane potential-sensitive fluorescent dyes. This invention fulfills this and related needs.

The thiobarbituric acid-based oxonols, often referred to as "DiSBAC" dyes (in the case of symmetric thiobarbituric acid-derived polymethine oxonols) form a family of spectrally distinct potentiometric probes with excitation maxima covering most range of visible wavelengths. $DiSBAC_2(3)$ has been the most popular oxonol dye for membrane potential measurement [Plasek J, Sigler K. "Slow fluorescent indicators of membrane potential: a survey of different approaches to probe response analysis." *J Photochem Photobiol B* 33, 101-124 (1996); Loew L M. "Characterization of Potentiometric Membrane Dyes." *Adv Chem Ser* 235, 151 (1994); Loew, L. M., "How to choose a potentiometric membrane probe", In *Spectroscopic Membrane Probes*. CRC Press, Boca Raton L., 1988, pp 139-151; Loew, L. M., "Potentiometric membrane dyes", In *Fluorescent and Luminescent Probes for Biological Activity*. W. T. Mason (editor), Academic Press, San Diego, 1993, pp 150-160]. These dyes enter depolarized cells where they bind to intracellular proteins or membranes and exhibit enhanced fluorescence. Increased depolarization results in more influx of the anionic dye and thus an increase in fluorescence.

In general, DiSBAC dyes bearing longer alkyl chains had been proposed to have better properties for measuring membrane potentials [Loew L M., "Potentiometric Membrane Dyes". In *Fluorescent and Luminescent Probes for Biological Activity*, Mason W T, 2.sup.nd Ed. 1999, pp 210-221; Gonzalez J E, Tsien R Y. "Improved indicators of cell membrane potential that use fluorescence resonance energy transfer." *Chem Biol* 4, 269-277 (1997)]. Recently this hypothesis has been disputed by the fact that $DiSBAC_1(3)$ possess better properties for optical measurement of membrane potentials than $DiSBAC_2(3)$ (U.S. Patent Application 20030087332). In this invention, $DiSBAC_6(3)$ and $DiSBAC_0(3)$ are prepared to confirm the existing theories of designing effective fluorescent indicators for measuring membrane potentials. Neither of the compounds prove to be better fluorescent indicators for measuring membrane potentials than $DiSBAC_1(3)$ although $DiSBAC_0(3)$ or $DiSBAC_6(3)$ would have been a better fluorescent membrane potential indicator [than $DiSBAC_1(3)$] according to U.S. Patent Application 20030087332 or according to the generally accepted hypothesis that more hydrophobic oxonols tend to be better fluorescent membrane potential indicators.

The existing thiobarbituric acid-derived polymethine oxonols used in optical measurement of membrane potentials are symmetric oxonols that are referred as 'DiSBAC' and have the four same alkyl groups on the two thiobarbituric acid moieties. In our previous disclosure (U.S. patent application Ser. No. 10/971,311) we discovered that the thiobarbituric acid-derived polymethine oxonols with moderate hydrophobicity tend to be sensitive fluorescent indicators for optical measurement of membrane potentials, and to be less prone to effects of extracellular environmental changes, e.g. culture medium and temperature etc. The substitutes on the nitrogen atoms of two thiobarbituric acid moieties need be critically fine-tuned. As a continuation-in-part to U.S. patent application Ser. No. 10/971,311 this invention provides an improved method for optical measurement of membrane potentials by using N,N,N'-trialkyl thiobarbituric acid-derived polymethine oxonols that have minimal serum effect compared to the existing N,N,N',N'-tetraalkyl thiobarbituric acid-derived polymethine oxonols. The typical N,N,N'-trialkyl oxonols are generally prepared as shown in FIG. 1.

REFERENCES CITED

U.S. patent Documents

| | | |
|---|---|---|
| 20030100059 (App. No.) | May 29, 2003 | Yao Y et al. |
| 20030087332 (App. No.) | May 8, 2003 | Klaubert et al. |
| 4,560,665 | December 1985 | Nakae et al. |
| 4,861,727 | August 1989 | Hauenstein et al. |
| 4,900,934 | February 1990 | Peeters et al. |
| 5,244,813 | September 1993 | Walt et al. |
| 5,661,035 | August 1997 | Tsien et al. |
| 6,107,066 | August 2000 | Tsien et al. |

Foreign Patent Documents

| | | |
|---|---|---|
| 137515 | October 1984 | EP. |
| 397641 | April 1990 | EP. |
| 429907 | November 1990 | EP. |
| 520262 | June 1992 | EP. |
| 552107 | January 1993 | EP. |
| WO9508637 | March 1995 | WO. |
| WO9527204 | October 1995 | WO. |
| WO 96/41166 | December 1996 | WO |
| WO 98/30715 | July 1998 | WO. |

OTHER PUBLICATIONS

Burgstahler R, Koegel H, Rucker F, Tracey D, Grafe P, Alzheimer C. "Confocal ratiometric voltage imaging of cultured human keratinocytes reveals layer-specific responses to ATP." Am J Physiol Cell Physiol 284, C944-52 (2003).

Coclet-Ninin J, Rochat T, Poitry S, Chanson M. "Discrimination between cystic fibrosis and CFTR-corrected epithelial cells by a membrane potential-sensitive probe." Exp Lung Res 28, 181-199 (2002).

Baxter D F, Kirk M, Garcia A F, Raimondi A, Holmqvist M H, Flint K K, Bojanic D, Distefano P S, Curtis R, Xie Y. "A novel membrane potential-sensitive fluorescent dye improves cell-based assays for ion channels." J Biomol Screen 7, 79 (2002).

Falconer M, Smith F, Surah-Narwal S, Congrave G, Liu Z, Hayater P, Ciaramella G, Keighley W, Haddock P, Waldron G, Sewing A. "High-throughput screening for ion channel modulators" J Biomol Screen 7, 460 (2002).

Adkins C E, Pillai G V, Kerby J, Bonnert T P, Haldon C, McKernan R M, Gonzalez J E, Oades K, Whiting P J, Simpson P B. "alpha4beta3delta GABA(A) receptors characterized by fluorescence resonance energy transfer-derived measurements of membrane potential." J Biol Chem 276, 38934-9 (2001).

Suh B C, Kim J S, Namgung U, Ha H, Kim K T. "P2x(7) nucleotide receptor mediation of membrane pore formation and superoxide generation in human promyelocytes and neutrophils." J Immunol 166, 6754-6763 (2001).

Cacciatore T W, Brodfuehrer P D, Gonzalez J E, Jiang T, Adams S R, Tsien R Y, Kristan W B Jr, Kleinfeld D. "Identification of neural circuits by imaging coherent electrical activity with FRET-based dyes." Neuron 23, 449-459 (1999).

Gonzalez J E, Tsien R Y. "Improved indicators of cell membrane potential that use fluorescence resonance energy transfer." Chem Biol 4, 269-277 (1997).

Dall'Asta V, Gatti R, Orlandini G, Rossi P A, Rotoli B M, Sala R, Bussolati O, Gazzola G C. "Membrane potential changes visualized in complete growth media through confocal laser scanning microscopy of bis-oxonol-loaded cells." Exp Cell Res 231, 260-268 (1997). Marriott I, Mason M J. "Evidence for a phorbol ester-insensitive phosphorylation step in capacitative calcium entry in rat thymic lymphocytes." J Biol Chem 271, 26732-26738.

Rader R K, Kahn L E, Anderson G D, Martin C L, Chinn K S, Gregory S A. "T cell activation is regulated by voltage-dependent and calcium-activated potassium channels." J Immunol 156, 1425-1430 (1996).

Ferrari D, Villalba M, Chiozzi P, Falzoni S, Ricciardi-Castagnoli P, Di Virgilio F. "Mouse microglial cells express a plasma membrane pore gated by extracellular ATP." J Immunol 156, 1531-1539 (1996).

Plasek J, Sigler K. "Slow fluorescent indicators of membrane potential: a survey of different approaches to probe response analysis." J Photochem Photobiol B 33, 101-124 (1996).

Amoroso S, Iannotti E, Saggese M L, Di Renzo G, Annunziato L. "The A1 agonist CCPA reduced bisoxonol-monitored membrane potential depolarization elicited by high K+ in cerebrocortical nerve endings." Biochim Biophys Acta 1239, 67-73 (1995).

Verkman A S. "Optical methods to measure membrane transport processes." J Membr Biol 148, 99-110 (1995).

Loew L M. "Characterization of Potentiometric Membrane Dyes." Adv Chem Ser 235, 151 (1994).

Kim W K, Rabin R A. "Characterization of the purinergic P2 receptors in PC12 cells. Evidence for a novel subtype." J Biol Chem 269, 6471-6477 (1994).

Dall'Asta V, Rossi P A, Bussolati 0, Gazzola G C. "Response of human fibroblasts to hypertonic stress. Cell shrinkage is counteracted by an enhanced active transport of neutral amino acids." J Biol Chem 269, 10485-10491 (1994).

Cabado A G, Vieytes M R, Botana L M. "Effect of ion composition on the changes in membrane potential induced with several stimuli in rat mast cells." J Cell Physiol 158, 309-316 (1994).

Shapiro H M. "Cell membrane potential analysis." Methods Cell Biol 41, 121-133 (1994).

Tanner M K, Wellhausen S R, Klein J B. "Flow cytometric analysis of altered mononuclear cell transmembrane potential induced by cyclosporin." Cytometry 14, 59-69 (1993).

Lukacs G L, Chang X B, Bear C, Kartner N, Mohamed A, Riordan J R, Grinstein S. "The delta F508 mutation decreases the stability of cystic fibrosis transmembrane conductance regulator in the plasma membrane. Determination of functional half-lives on transfected cells." J Biol Chem 268, 21592-21598 (1993).

Schwartz M A. "Spreading of human endothelial cells on fibronectin or vitronectin triggers elevation of intracellular free calcium." J Cell Biol 120, 1003-1010 (1993).

Loew L M. "Confocal microscopy of potentiometric fluorescent dyes." Methods Cell Biol 38, 195-209 (1993).

Seamer L C, Mandler R N. "Method to improve the sensitivity of flow cytometric membrane potential measurements in mouse spinal cord cells." Cytometry 13, 545-552 (1992).

Bronner C, Landry Y. "The use of the potential-sensitive fluorescent probe bisoxonol in mast cells." Biochim Biophys Acta 1070, 321-331 (1991).

Taglialatela M, Canzoniero L M, Fatatis A, Di Renzo G, Yasumoto T, Annunziato L. "Effect of maitotoxin on cytosolic $Ca^{2+}$ levels and membrane potential in purified rat brain synaptosomes." Biochim Biophys Acta 1026, 126-132 (1990).

Pittet D, Di Virgilio F, Pozzan T, Monod A, Lew D P. "Correlation between plasma membrane potential and second messenger generation in the promyelocytic cell line HL-60." J Biol Chem 265, 14256-14263 (1990).

Freedman J C, Novak T S. "Optical measurement of membrane potential in cells, organelles, and vesicles." Methods Enzymol 172, 102-122 (1989).

Sahlin S, Hed J, Rundquist I. "Differentiation between attached and ingested immune complexes by a fluorescence quenching cytofluorometric assay." J. Immunol. Methods. 60, 115-124 (1983).

SUMMARY OF THE INVENTION

Conventional electrophysiological techniques (the so called 'Patch Clamping' recording) use an electrode to measure membrane potentials. The electrical method is not only invasive, but also limited to measurement of membrane potentials in a single cell. By contrast, the optical indicators described herein are particularly advantageous for simultaneously monitoring the membrane potential of a population of cells, e.g., many neurons or muscle cells. Optical indicators, unlike conventional microelectrodes, do not require physical puncture of the membrane. In many cells or organelles, such puncture is highly injurious or mechanically difficult to accomplish although some automated 'Patch Clamping' technologies have been developed in recent years. The optical indicators are still most suitable for cells too small or fragile to be impaled by electrodes.

This invention provides improved optical methods and compositions for determining transmembrane electrical potential (membrane potential), particularly across the outermost (plasma) membrane of living cells. In one aspect, the method comprises: (a) contacting a fluorescent thiobarbituric acid-derived polymethine oxonol with cells. The fluorescent indicator is capable of redistributing from a first face of the membrane to a second face of the membrane in response to changes in the potential of the membrane (as determined by the Nernst equation); (b) exposing the membrane-containing structure to excitation light of an appropriate wavelength, typically in the ultraviolet or visible region; and (c) relating the fluorescence intensity to the membrane potential.

In another aspect of the invention, the voltage sensing methods allow one to detect the effect of test samples, such as potential therapeutic drug molecules, on the activation/deactivation of ion transporters (channels, pumps, or exchangers) embedded in the membrane.

BRIEF DESCRIPTION OF THE DRAWINGS

The invention may be better understood with reference to the accompanying drawings.

Figure 1:
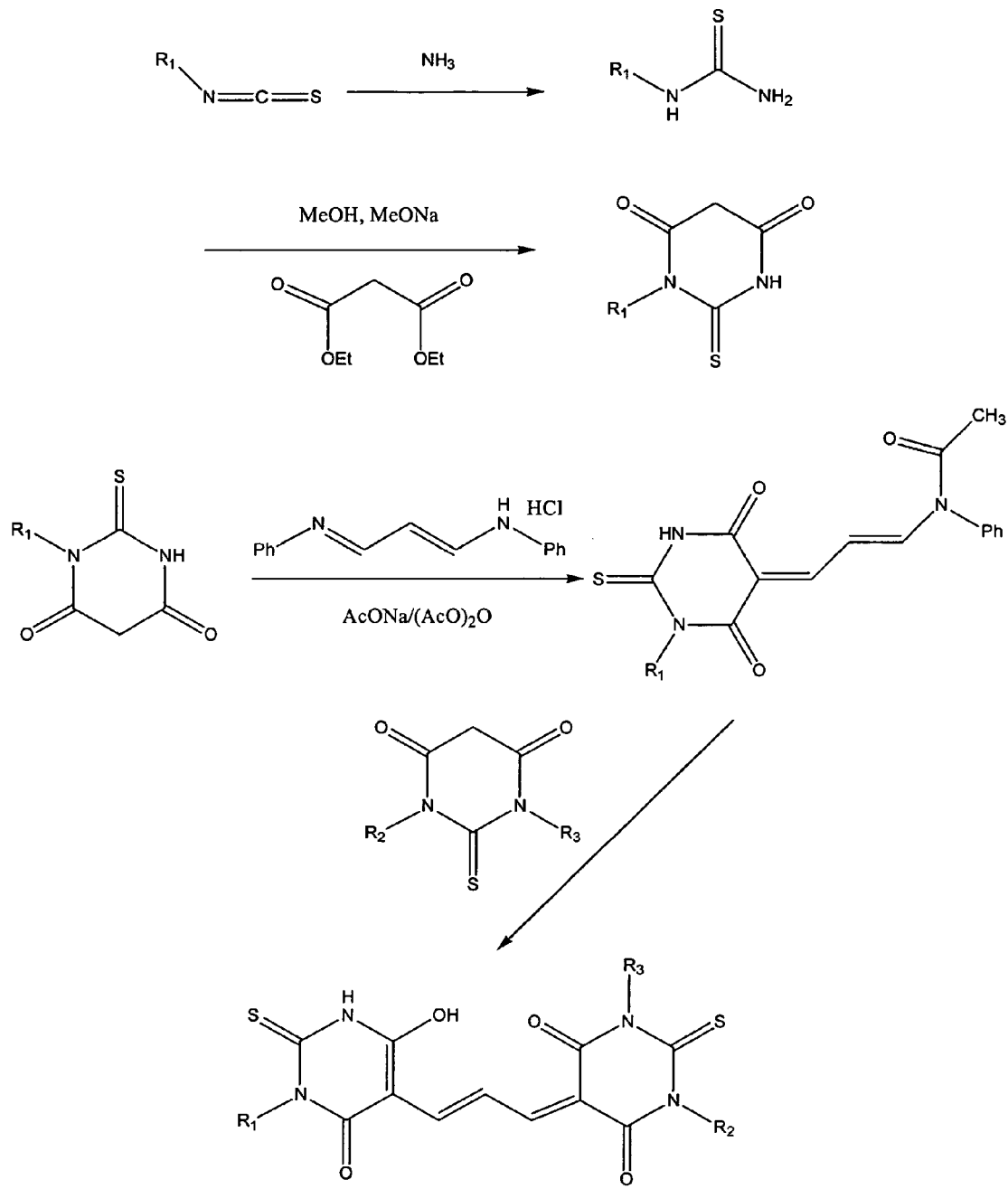
FIG. 1. The typical synthesis of N,N,N'-trialkyl thiobarbituric acid-derived polymethine oxonols.
Figure 2:
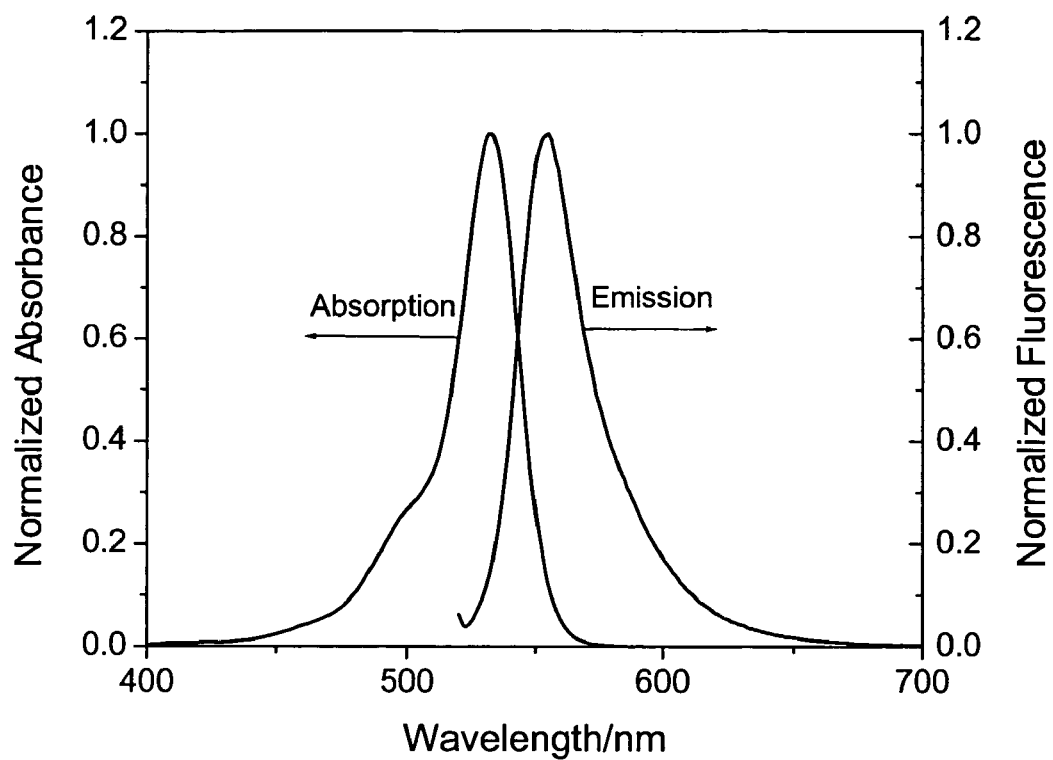
FIG. 2. The absorption and fluorescence spectra of Compound 4, a representative N,N,N'-trialkyl thiobarbituric acid-derived polymethine oxonol in methanol.

The HTR7B-CNG cells cultured in serum-free medium was loaded with Compound 4 (30 μM) or DiSBAC$_2$ (3) (30 μM) solution for 2 hr. The serial diluted 5-HT is added into the cells to stimulate human 5-hydroxytryptamine receptor 7B. The fluorescence signals of Compound 4 and DiSBAC$_2$(3) are recorded before adding 5-HT ($F_0$) or 30 minutes after adding 5-HT (F). The $F/F_0$ is calculated and plotted versus the concentration of 5-HT (n=4, mean±SD).

DESCRIPTION OF THE PREFERRED EMBODIMENT

The following definitions are set forth to illustrate and define the meaning and scope of the various terms used to describe the invention herein.

The term "hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "alkyl" refers to a branched or straight chain acyclic, monovalent saturated hydrocarbon radical of one to twenty carbon atoms. This term is further exemplified by radicals such as methyl, ethyl, n-propyl, i-propyl, n-butyl, i-butyl, sec-butyl, t-butyl, n-pentyl, 2-methyl butyl, 3-methyl butyl, and 2-ethyl propyl.

The term "alkenyl" refers to an unsaturated hydrocarbon radical which contains at least one carbon-carbon double bond and includes straight chain, branched chain and cyclic radicals. This term is further exemplified by radicals such as ethenyl, propenyl, 1-butenyl, 3-methyl-1-butenyl, cyclopentenyl and cyclohexenyl.

The term "alkynyl" refers to an unsaturated hydrocarbon radical which contains at least one carbon-carbon triple bond and includes straight chain, branched chain and cyclic radicals. This term is further exemplified by radicals such as ethynyl, propynyl, 1-butynyl, 2-butynyl, 3-methyl-1-butynyl, and 3-methyl-1-pentynyl.

The term "heteroalkyl" refers to a branched or straight chain acyclic, monovalent saturated radical of two to forty atoms in the chain in which at least one of the atoms in the chain is a heteroatom, such as, for example, oxygen, nitrogen or sulfur. This term is further exemplified by radicals such as OCH$_3$, NHCH$_3$, N(CH$_3$)$_2$, SCH$_3$, CH$_2$OH, CH$_2$NH$_2$, CH$_2$SH, CH$_2$OCH$_3$, CH$_2$NHCH$_3$, CH$_2$N(CH$_3$)$_2$, CH$_2$SCH$_3$, CH$_2$CH$_2$OH, CH$_2$CH$_2$NH$_2$, CH$_2$CH$_2$NH(CH$_3$), CH$_2$CH$_2$N(CH$_3$)$_2$, and CH$_2$CH$_2$SH.

The term "cycloalkyl" refers to a monovalent saturated carbocyclic radical of three to twelve carbon atoms in the carbocycle. This term is further exemplified by radicals such as cyclopropyl, cyclobutyl, cyclopentyl, and cyclohexyl.

The term "heterocycloalkyl" refers to a monovalent saturated cyclic radical of one to twelve atoms in the ring, having at least one heteroatom, such as oxygen or sulfur within the ring. This term is further exemplified by radicals such as epoxidyl, aziridinyl, tetrahydrofuranyl, tetrahydropyrroleyl, tetrahydrothiopheneyl, and morpholinyl.

The term "alkylene" refers to a fully saturated, cyclic or acyclic, divalent, branched or straight chain hydrocarbon radical of one to forty carbon atoms. This term is further exemplified by radicals such as methylene, ethylene, n-propylene, 1-ethylethylene, and n-heptylene.

The term "heteroalkylene" refers to an alkylene radical in which at least one of the atoms in the chain is a heteroatom. This term is further exemplified by radicals such as NHCH$_2$CHCH$_2$, OCH$_2$CHCH$_2$, SCH$_2$CHCH$_2$, CH$_2$NHCH$_2$CHCH$_2$, CH$_2$OCH$_2$CHCH$_2$, CH$_2$SCH$_2$CHCH$_2$, CH$_2$NHCH$_2$CHCHCH$_3$, CH$_2$OCH$_2$CHCHCH$_3$, and CH$_2$SCH$_2$CHCHCH$_3$.

The term "substituted phenyl" refers to a phenyl group which is mono-, di-, tri-, tetra or penta-substituted, independently, with hydrocarbyl, alkyl, lower-alkyl, cycloalkyl or cycloalkyl-lower alkyl. This term is further exemplified by radicals such as PhCH$_3$, Ph(CH$_3$)$_2$, Ph(CH$_3$)$_3$, PhC$_2$H$_5$, Ph(CH$_3$)(C$_2$H$_5$), Ph(C$_2$H$_5$)$_2$, and PhC$_3$H$_5$.

The term "aryl" refers to an aromatic monovalent carbocyclic radical having a single conjugated ring (e.g., phenyl) or multiple condensed and conjugated rings (e.g., naphthyl, anthracenyl), which can optionally be mono-, di-, tri- or tetra-substituted, independently, with hydrocarbyl, alkyl, lower-alkyl, cycloalkyl or cycloalkyl lower alkyl.

The term "halo" refers to fluoro, bromo, chloro and iodo.

The term "polymethine oxonol" refers to molecules comprising two potentially acidic groups linked via a polymethine chain and possessing a single negative charge delocalized between the two acidic groups. The preferred acidic groups are thiobarbiturates.

The term "N,N,N'-trialkyl thiobarbituric acid-derived oxonols" referes to thiobarbituric acid-containing oxonols in which one of the substituents on the nitrogen atoms of thiobarbiturate moieties is hydrogen.

The term "slightly hydrophobic" when used in the context of the hydrophobic ion refers to a species whose partition coefficient between a physiological saline solution (e.g. HBSS) and octanol is between 5 and 1000, preferably at least about 20 and 500. Methods of determining partition coefficients and adsorption coefficients are known to those of skill in the art.

Oxonol compounds used in this invention have a general structure of Formula I.

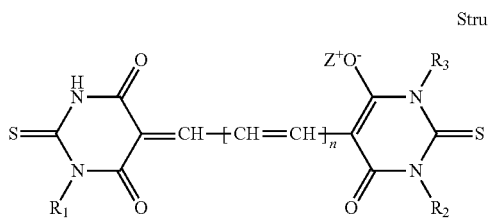

Structure I wherein R1, R2, and R3 are independently selected from the group consisting of alkyl, haloalkyl and heteroalkyl. n is an integer from 1 to 3; Z is Na, K, ammonium or other biologically acceptable salt. Oxonols in which the R groups on a particular thiobarbiturate moiety are different to each other are specifically contemplated by this invention and can be prepared from urea derivatives as described in FIG. 1 via the corresponding intermediates of Structure II.

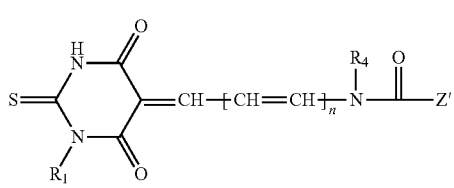

Structure II wherein R1 and R4 are independently selected from the group consisting of hydrogen, hydrocarbyl, preferably alkyl, haloalkyl and heteroalkyl; n is an integer from 1 to 3; Z' is a hydrocarbyl group. Preferably R4 is phenyl, and Z' is methyl or trifluoromethyl.

The compositions of the present invention comprise an N,N,N'-trialkyl thiobarbituric acid-derived polymethine for optical measurement of membrane potentials. The fluorescent reagent comprises a slightly hydrophobic anion which is capable of redistributing from one face of a membrane to the other in response to changes in transmembrane potential. This anion is referred to as the mobile or slightly hydrophobic anion. The slightly hydrophobic ion is an anion which labels the extracellular face of the plasma membrane. Upon addition of the slightly hydrophobic fluorescent anion to the membrane, cell, or tissue preparation, the anion partitions into the plasma membrane, where it distributes between the extracellular and intracellular surfaces according to a Nernstian equilibrium. Changes in the membrane potential cause the fluorescent anion to migrate across the membrane so that it can continue to bind to whichever face (the intracellular or extracellular face) is now positively charged. The fluorescence intensity is a function of intracellular concentration of the hydrophobic ion and this concentration varies as the fluorescent anion redistributes back and forth across the membrane depending the membrane potential.

The measurement of fluorescence intensity provides a sensitive method for monitoring changes in the transmembrane potential. For example, if the membrane potential (intracellular relative to extracellular) changes from negative to positive, the fluorescent hydrophobic anion is pulled from the extracellular surface to the intracellular surface of the plasma membrane. This results in an increase in fluorescence intensity. Thus, fluorescence measurements at appropriate excitation and emission wavelengths provide a fluorescence readout which is sensitive to the changes in the transmembrane potential. Typically, the time constant for the redistribution of the fluorescent anion is rapid and in the millisecond to second time scale thus allowing the convenient measurement of both rapid cellular electrical phenomena such as action potentials or ligand-evoked channel opening and slower and more sustained changes evoked by altering the activity of ion pumps or exchangers.

On one aspect the detection method comprises: (a) introducing a first reagent comprising a slightly hydrophobic polymethine anion capable of redistributing from a first face of the membrane to a second face of the membrane in response to changes in the potential of the membrane; (b) exposing the membrane to excitation light of appropriate wavelengths; (c) measuring fluorescence intensity of the polymethine indicator; and (d) relating the energy transfer to the change in plasma membrane potential.

N,N,N'-trialkyl thiobarbituric acid-derived polymethine oxonols serve as a voltage sensor and move within the membrane from one face of the membrane to another in response to changes in the transmembrane potential. The distribution of hydrophobic ions between the two membrane-aqueous interfaces (the extracellular interface and the intracellular interface) is determined by the membrane potential. Cations will tend to congregate at the negatively charged membrane interface and correspondingly, anions will move to the positively charged interface. The inherent sensitivity of the invention is based on the large interfacial concentration changes of the mobile ion at physiologically relevant changes in membrane potentials. The methods of this invention couple this change in interfacial concentration to an efficient fluorescence readout thus providing a sensitive method of detecting changes in transmembrane potential. The speed of the fluorescence change is dependent on the membrane translocation rate of the slightly hydrophobic ion.

One aspect of the present invention provides N,N,N'-trialkyl thiobarbituric acid-derived anionic dyes which translocate across the membrane at much faster rates. The indicators of the present invention are also able to follow slower voltage changes over a time scale of seconds to minutes. It is generally preferred that the hydrophobic dye be an anionic species. Ester groups of biological membranes generate a sizable dipole potential within the hydrocarbon core of the membrane. This potential aids anion translocation through the hydrophobic layer but hinders cations. Therefore, where membrane translocation is concerned, anions have a tremendous inherent speed advantage over cations. For example, it is known that for the isostructural ions tetraphenylphosphonium cation and tetraphenylborate anion, the anion is much more permeable than the cation (Flewelling, R. F. and Hubbell, W. L. 1986. "The membrane dipole potential in a total membrane potential model", Biophys. J. 49:541-552).

Preferably, the fluorescent ions which translocate across the plasma membrane are slightly hydrophobic in order to bind strongly to the plasma membrane and translocate rapidly across it in response to changes in transmembrane potential. Preferably, the ion will have a single charge which will be delocalized across a significant portion of the dye, preferably the entire dye. An oxonol's negative charge is distributed over the entire chromophore. Compound 4 absorbs at 532 nm (ext. coefficient=175,000 $M^{-1}$ $cm^{-1}$), emits at 555 nm and has a quantum yield of >0.2 in octanol. Increasing hydrophobicity minimizes release of the bound dye from the plasma membrane and buries the ion deeper into the membrane, which decreases the electrostatic activation energy for translocation. However, hydrophobicity cannot be increased without limit, because some aqueous solubility is required to permit cellular loading. This invention reveals that highly hydrophobic polymethine oxonols tend to give high assay background probably due to poor water solubility and serum binding. If necessary, the oxonol dyes may be loaded with the aid of amphiphilic solubilizing reagents such as beta-cyclodextrin, Pluronics such as Pluronic F-127, or polyethylene glycols such as PEG400, which help solubilize the hydrophobic ions in aqueous solution. Polar groups on the ion should be kept to a minimum and shielded as much as possible to disfavor solvation in the head group region of the bilayer. In this invention, slightly hydrophobic thiobarbituric acid-derived polymethine oxonols are developed to have the optimized properties for optical measurement of membrane potentials while minimizing the serum effect.

An extremely useful property of these oxonols is that their fluorescence intensity is 5-30 times brighter when bound to membranes than in aqueous solution [Rink, T. J., Montecucco, C., Hesketh, T. R., and Tsien, R. Y. 1980. "Lymphocyte membrane potential assessed with fluorescent probes." Biochim. Biophys. Acta 595, 15-30]. Furthermore, the negative charge is delocalized throughout the chromophore with the four equivalent oxygens containing the majority of the charge. The high electron affinity of the thiobarbiturate moieties discourages protonation, pKa<1, and resists photooxidative bleaching. The three N-alkyl groups and the thiocarbonyl give the molecule a necessary amount of hydrophobicity needed for tight membrane binding and rapid translocation while maintaining proper water solubility.

Figure 3:
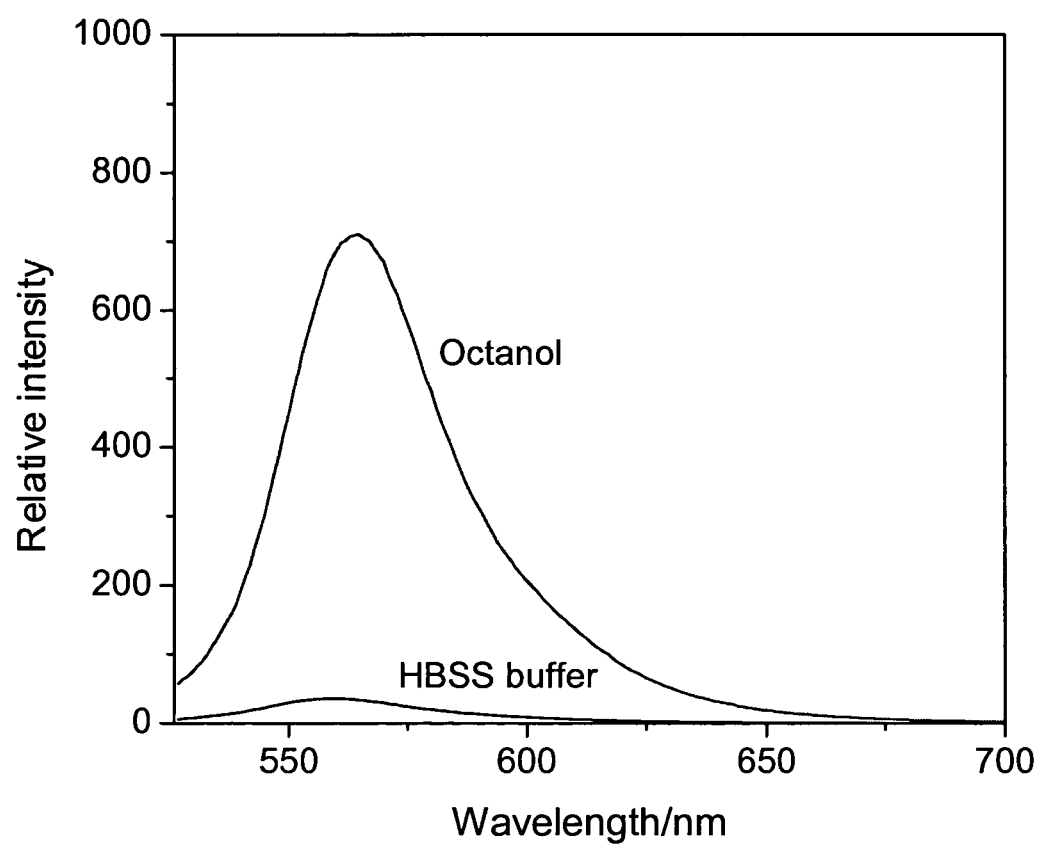
FIG. 3. The fluorescence comparison of Compound 4 (a representative N,N,N'-trialkyl thiobarbituric acid-derived polymethine oxonol) in HBSS buffer and octanol.

Preferably, the anions should be strongly fluorescent when adsorbed to the membrane, whereas they should have minimal fluorescence when free in aqueous solution. Preferably, the anionic fluorophores should be at least 2 times, and more preferably at least about 4 times, brighter when adsorbed to the membrane. In the case of the thiobarbituric oxonols described herein, their fluorescence is about 3-30 fold greater in the membrane than in water (see FIG. 3). In principle, if the dye bound extremely tightly to the membrane one would not need a high ratio of fluorescence when bound to the membrane to that when free in aqueous solution. However, it is desirable for the membrane potential-sensitive indicators to be at least about four times more strongly fluorescent in a membrane than in aqueous solution because in reality the volume of the membrane is tiny relative to the aqueous solution and some water solubility is necessary for loading of the dye into cells and tissue.

The anions also should not act as ionophores, especially protonophores, since such behavior may generate sustained leakage currents. Therefore, the protonation pKa of the anion is typically well below 7, preferably below 5, more preferably below 3. Red to infra-red wavelengths of excitation and emission are preferred to avoid tissue scattering and heme absorbances. Photodynamic damage should be kept as low as possible, probably best by minimizing triplet state formation and the resulting generation of singlet oxygen.

On another aspect of the present invention the detection method comprises: (a) introducing a first reagent comprising a slightly hydrophobic polymethine anion capable of redistributing from a first face of the membrane to a second face of the membrane in response to changes in the potential of the membrane; (b) introducing a second reagent which labels the first face or the second face of the membrane, which second reagent comprises a fluorophore capable of undergoing energy transfer by either (i) donating excited state energy to the fluorescent anion, or (ii) accepting excited state energy from the fluorescent anion; (c) exposing the membrane to excitation light of appropriate wavelengths; (d) measuring energy transfer between the fluorescent anion and the second reagent; and (e) relating the energy transfer to the change in plasma membrane potential.

The preferred mode of energy transfer is fluorescence resonance energy transfer (FRET). The method finds particular utility in detecting changes in membrane potential of the plasma membrane in biological cells. The first and second reagents are spectroscopically complementary to each other, by which is meant that their spectral characteristics are such that excited state energy transfer can occur between them. Either reagent can function as the donor or the acceptor, in which case the other reagent is the corresponding complement, i.e., the acceptor or donor respectively. Both FRET and quenching are highly sensitive to the distance between the two species. For example, the non-radiative Forster-type quenching observed in FRET varies inversely with the sixth power of the distance between the donor and acceptor species. Therefore, when the membrane potential changes and the hydrophobic fluorescent anion moves either further away from or closer to the second reagent, FRET between the two reagents is either reduced or enhanced significantly. Other mechanisms such as electron-transfer, Dexter exchange interaction, paramagnetic quenching, and promoted intersystem crossing are even shorter-range and require the two reagents to collide or at least come within 1 nm of each other.

In one class of embodiments of the present invention, the slightly hydrophobic ion that fluorescences on one face of the membrane is quenched by a mechanism other than FRET. FRET has the advantages of working over long distances, which minimizes the necessary concentration of acceptors, and of giving ratiometric output at two emission wavelengths. However, if FRET is too efficient over very long distances greater than the thickness of the membrane, it can fail to discriminate between acceptors on the same vs. opposite sides of the membrane. The other mechanisms of quenching are much shorter-range and should never be effective across the thickness of the membrane.

FRET or fluorescence quenching is best detected by emission ratio which can distinguish the two populations of the mobile fluorophore, i.e, those bound to the extracellular vs. those bound to the intracellular face of the membrane. In particular, FRET using a fluorescent acceptor provides an emission ratio change that is well suited to laser-scanning confocal microscopy and internally corrects for variations in donor loading, cell thickness and position (including motion artifacts), and excitation intensity. Emission ratios usually change by larger percentages than either emission wavelength signal alone, because the donor and acceptor emissions should change in opposite directions, which reinforce each other when ratioed. If emission ratioing is not desirable or possible, either wavelength can still be used alone, or the change in donor excited-state lifetime monitored.

High sensitivity is achieved when the voltage sensor, i.e., the polymethine oxonols, translocates at least a full unit charge nearly all the way through the membrane. Even without specific ion channels or transporters, such translocation can be quite rapid if the ion is negatively charged, delocalized, and slightly hydrophobic. However, voltage sensing should not require further diffusion of the ion through the unstirred aqueous layers that slows the response and generates a sustained leakage current.

To create an optical readout from the translocation of the slightly hydrophobic oxonol anion (i.e., the first reagent) from one side of the plasma membrane to the other side, FRET or fluorescence quenching between the translocating ion and a fluorophore or quencher (i.e., the second reagent)

fixed to just one face of the plasma membrane is employed. Most conveniently, the extracellular face is employed.

Single cells were used in the examples so that the optical signals could be compared with voltage changes accurately known from traditional microelectrode techniques, such as patch clamping, which are applicable only to single cells. However, it should be apparent that the dyes can be used for many applications in which microelectrodes are not applicable. Comparison with microelectrodes is needed merely for accurate calibration and proof that the mechanism of fluorescence signal generation is as described herein. The reagent compositions and methods described herein can either resolve the different electrical potentials of many neighboring cells or neighboring parts of a single cell, or give an average reading for all the membrane locations, depending on whether the optical signal is spatially imaged or pooled.

The methods described herein are applicable to a wide variety of membranes. In particular, membrane potentials in membranes of biological cells can be detected and monitored. The method finds greatest utility with plasma membranes, especially the outermost plasma membrane of mammalian cells. Representative membranes include, but are not limited to, subcellular organelles, membranes of the endoplasmic reticulum, secretory granules, mitochondria, microsomes and secretory vesicles. Cell types which can be used include but are not limited to, neurons, cardiac cells, lymphocytes (T and B lymphocytes), nerve cells, muscle cells and the like.

The invention also provides methods for screening test samples such as potential therapeutic drugs which affect membrane potentials in biological cells. These methods involve measuring membrane potentials as described above in the presence and absence (control measurement) of the test sample. Control measurements are usually performed with a sample containing all components of the test sample except for the putative drug. Detection of a change in membrane potential in the presence of the test agent relative to the control indicates that the test agent is active. Membrane potentials can also be determined in the presence or absence of a pharmacologic agent of known activity (i.e., a standard agent) or putative activity (i.e., a test agent). A difference in membrane potentials as detected by the methods disclosed herein allows one to compare the activity of the test agent to that of the standard agent. It will be recognized that many combinations and permutations of drug screening protocols are known to one of skill in the art and they may be readily adapted to use with the method of membrane potential measurement disclosed herein to identify compounds which affect membrane potentials.

Use of the membrane potential determination technique disclosed herein in combination with all such methods are contemplated by this invention. In a particular application, the invention offers a method of identifying a compound which modulates activity of an ion channel, pump, or exchanger in a membrane, comprising: (a) loading the cells with the N,N,N'-trialkyl thiobarbituric acid-derived polymethine oxonols; (b) determining the membrane potential as described above; (c) exposing the cells to the test sample; (d) redetermining the membrane potential and comparing with the result in (b) to determine the effect of the test sample; (e) optionally, exposing the membrane to a stimulus which modulates an ion channel, pump or exchanger, and redetermining the membrane potential and comparing with the result in (d) to determine the effect of the test sample on the response to the stimulus.

In another application, the invention offers a method of screening test samples to identify a compound which modulates the activity of an ion channel, pump or exchanger in a membrane, comprising: (a) loading a first set and a second set of cells with the voltage-sensitive oxonols which measure membrane potential; (b) optionally, exposing both the first and second set of cells to a stimulus which modulates the ion channel, pump or exchanger; (c) exposing the first set of cells to the test sample; (d) measuring the membrane potential in the first and second sets of cells; and (e) relating the difference in membrane potentials between the first and second sets of cells to the ability of a compound in the test sample to modulate the activity of an ion channel, pump or exchanger in a membrane.

Ion channels of interest include, but are not limited to, sodium, calcium, potassium, nonspecific cation, and chloride ion channels, each of which may be constitutively open, voltage-gated, ligand-gated, or controlled by intracellular signaling pathways.

Biological cells which can be screened include, but are not limited to primary cultures of mammalian cells, cells dissociated from mammalian tissue, either immediately or after primary culture. Cell types include, but are not limited to white blood cells (e.g. leukocytes), hepatocytes, pancreatic beta-cells, neurons, smooth muscle cells, intestinal epithelial cells, cardiac myocytes, glial cells, and the like. The invention also includes the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel) and methods for their expression in cell lines of interest are within the knowledge of one of skill in the art (see, U.S. Pat. No. 5,436,128). Representative cultured cell lines derived from humans and other mammals include LM (TK.sup.−) cells, HEK293 (human embryonic kidney cells), 3T3 fibroblasts, COS cells, CHO cells, RAT1 and HLHepG2 cells.

The screening methods described herein can be made on cells growing in or deposited on solid surfaces. A common technique is to use a microtiter plate well wherein the fluorescence measurements are made by commercially available fluorescent plate readers. The invention includes high throughput screening in both automated and semiautomated systems. One such method is to use cells in Costar 96 well microtiter plates (flat with a clear bottom) and measure fluorescent signal with Flexstation plate reader (Molecular Devices Corp., CA) using a single wavelength to read fluorescence intensity or two emission wavelengths to record fluorescent emission ratios.

DETAILED DESCRIPTION OF THE INVENTION

The invention may be better understood with reference to the accompanying examples, which are intended for purposes of illustration only and should not be construed as in any sense limiting the scope of the invention as defined in the claims appended hereto.

Example 1

Synthesis of Compound 1

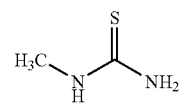

For all the syntheses, all starting materials and reagents were of the highest purity available (Aldrich Chemical Company, Milwaukee, Wis.) and used without further purification, except where noted. Solvents were HPLC grade (Fisher Scientific, Pittsburgh, Pa.) and were dried over activated molecular sieves. NMR spectra were acquired on a Varian Gemini 200 MHz spectrometer. Absorption and fluorescence spectra were taken respectively on a Cary 50 BIO and Varain Eclipse (Varian, Inc., Palo Alto, Calif.).

To ammonia in methanol (200 ml, 0.4 mol) methyl isothiocyanate (29.25 g, 0.4 mol) in THF (60 mL) is added proportion-wise under stirring in an ice/water bath. The reaction mixture is stirred at room temperature overnight, and TLC (hexane/ethyl acetate=1/1) is used to confirm the completion of the reaction. Solvent is removed in-vacuo and the residue is further dried under high vacuum to give a syrup. The residue is then mixed with hexane 300 (mL) and is stirred for 1 hour to give an off-white precipitate. The solid is collected by filtration, and washed with hexane (2×50 ml) to give an off-white solid (35 g, 97%).

Example 2

Synthesis of Compound 2

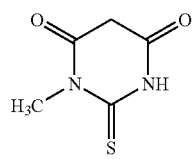

To anhydrous methanol (160 mL) is added sodium (9.2 g, 0.4 mol) in small piece with a setup of cooling condenser. During the addition the reaction mixture is spontaneously heated to reflux. After the sodium pellets are completely consumed, to the reaction mixture is added diethyl malonate (60.8 mL, 0.4 mol) in one portion, followed by adding N-methyl thiourea (18.03 g, 0.2 mol). The reaction mixture is refluxed overnight (22 h) and TLC (chloroform/methanol=7/3) is used to confirm the completion of the reaction. The solvent is removed in-vacuo, and the residue is dissolved in water (150 mL). The aqueous solution is acidified with 32% HCl to pH=2 under cooling. The formed light yellow solid is collected by filtration and air-dried. The dry solid is washed with hexane/ethyl acetate (1/1) until a white solid is obtained (19.0 g, 60%).

Example 3

Synthesis of Compound 3

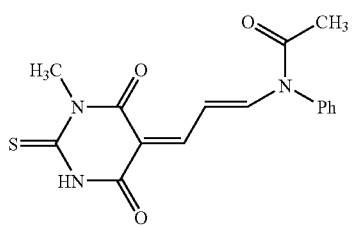

N-methyl thiobarbituric acid (1.58 g, 10 mmol), malonaldehyde dianil hydrochloride (2.59, 10 mmol) and sodium acetate (0.82 g, 10 mmol) in acetic andydride (15 mL) is refluxed for 20 min in an oil bath. The reaction mixture is cooled in an ice/water bath. To the formed precipitate is added 1:1 cold water/methanol (40 mL), and stirred. The precipitate is collected by filtration and then washed with methanol (3×10 mL) to give a dark brown solid that is dried under high vacuum to give the desired product (3.0 g).

Example 4

Synthesis of Compound 4

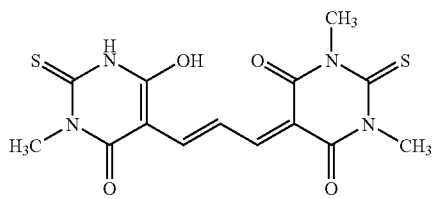

Compound 3 (2.9 g, 9 mmol) is suspended in acetonitrile (20 mL), and to the suspension N,N'-dimethyl thiobarbituric acid (1.55 g, 9 mmol) is added. To the reaction mixture is then added triethylamine (6.3 ml, 45 mmol), and stirred at room temperature for 4 h. TLC is used to confirm the completion of reaction. The formed purple precipitate is collected by filtration and washed with acetonitrile (3×5 mL). The crude product is further purified by column chromatorgraphy using a gradient of chloroform/methanol/triethylamine to give the desired product.

Example 5

Synthesis of Compound 5

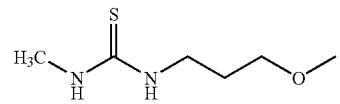

3-Methoxypropylamine is reacted with methylisothiocyanate according to the procedure of Compound 1 to give the desired product.

Example 6

Synthesis of Compound 6

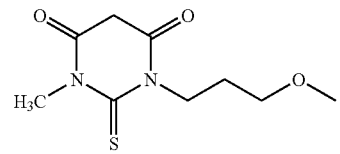

Compound 5 is reacted with diethyl malonate according to the procedure of Compound 2 to give the desired product.

Example 7

Synthesis of Compound 7

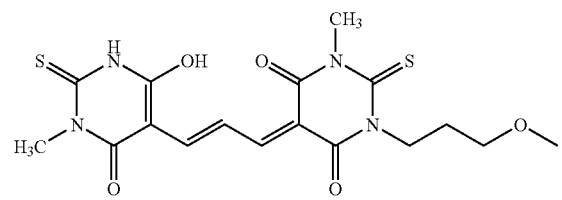

Compound 7 is prepared from Compounds 3 and 6 analogous to the procedure of Compound 4.

Other oxonols are made as illustrated in FIG. 1. Specifically the required barbiturates are prepared from the appropriate thiourea either prepared from required primary amine and carbon disulfide [Bortnick, N., Luskin, L. S., Hurwitz, M. D., and Rytina, A. W. 1956. t-Carbinamines, RR'R"CNH$_2$. III. The preparation of isocyanates, isothiocyanates and related compounds. J. Am. Chem. Soc. 78:4358-4361] or from the reactions of thiophosgen with the amines. The barbiturates are converted to the desired polymethine oxonols through the imine intermediates of Structure II.

Example 8

Water Solubility and Hydrophobicity Comparison of DiSBAC1(3) and Compounds 4 and 7

The thiobarbituric acid-derived polymethine oxonols are dissolved in DMSO (3 mM). The DMSO stock solutions are respectively partitioned in 1:1 octanol/HBSS buffer mixture. The concentrations of the oxonol dyes in octanol and aqueous layers are determined by absorption spectra. This invention concludes that the slightly hydrophobic compounds give the highest quality of assay data for measuring membrane potentials in cells.

Example 9

Measuring Membrane Potentials Using Compound 4 or 7

P2X2 belongs to a class of purinergic ion channels that pass calcium and sodium in response to purine, including adenosine 5'-triphosphate (ATP). The cells are 1321 N1 astrocytoma cells transfected to overexpress the purinergic P2X2 ligand-gated ion channel. Adapted from the published procedures [Baxter D F, Kirk M, Garcia A F, Raimondi A, Holmqvist M H, Flint K K, Bojanic D, Distefano P S, Curtis R, Xie Y. "A novel membrane potential-sensitive fluorescent dye improves cell-based assays for ion channels." J Biomol Screen 7, 79 (2002); Falconer M, Smith F, Surah-Narwal S, Congrave G, Liu Z, Hayater P, Ciaramella G, Keighley W, Haddock P, Waldron G, Sewing A. "High-throughput screening for ion channel modulators" J Biomol Screen 7, 460 (2002)], P2X2 cells are propagated and maintained in DME (high glucose), 10% FCS, Pen/Strep and 2 mM L-glutamine. The P2X2 cells are split at a 1 to 2 ratio upon confluence. 40,000 P2X2 cells are plated in 100 µL per well for 96 well plates or 10,000 P2X2 cells are plated in 25 µL per well for 384 well plates for overnight. Compound 4 or 7 is dissolved in DMSO. The DMSO stock solution is diluted with 20 mM HEPES (pH 7.40), incubated with the cells in HBSS buffer. The assay plates are incubated at 37° C. for 30-45 minutes. The fluorescence changes are recorded with a fluorescence microplate reader (preferably with an integrated liquid handling system), a microscope or a flow cytometer. An initial depolarization event is depicted as an increase in fluorescence followed by repolarization or decay in signal near baseline. EC50 should be in the range of 10-100 nM.

Example 10

Measurement of Membrane Potential with Compound 4 or 7 as FRET Acceptors and Fluorescent Lectins as FRET Donors Compound 4 or 7 is used to measure transmembrane potential in a FRET mode analogous to the procedure as described by Adkins C E, Pillai G V, Kerby J, Bonnert T P, Haldon C, McKernan R M, Gonzalez J E, Oades K, Whiting P J and Simpson P B. ["alpha4beta3delta GABA(A) receptors characterized by fluorescence resonance energy transfer-derived measurements of membrane potential." J Biol Chem 276, 38934-9 (2001)].

Example 11

Detection of cAMP-Dependent Activation of Cyclic Nucleotide-Gated Channels (CNG Channels) Using Compound 4 or 7

Figure 4:
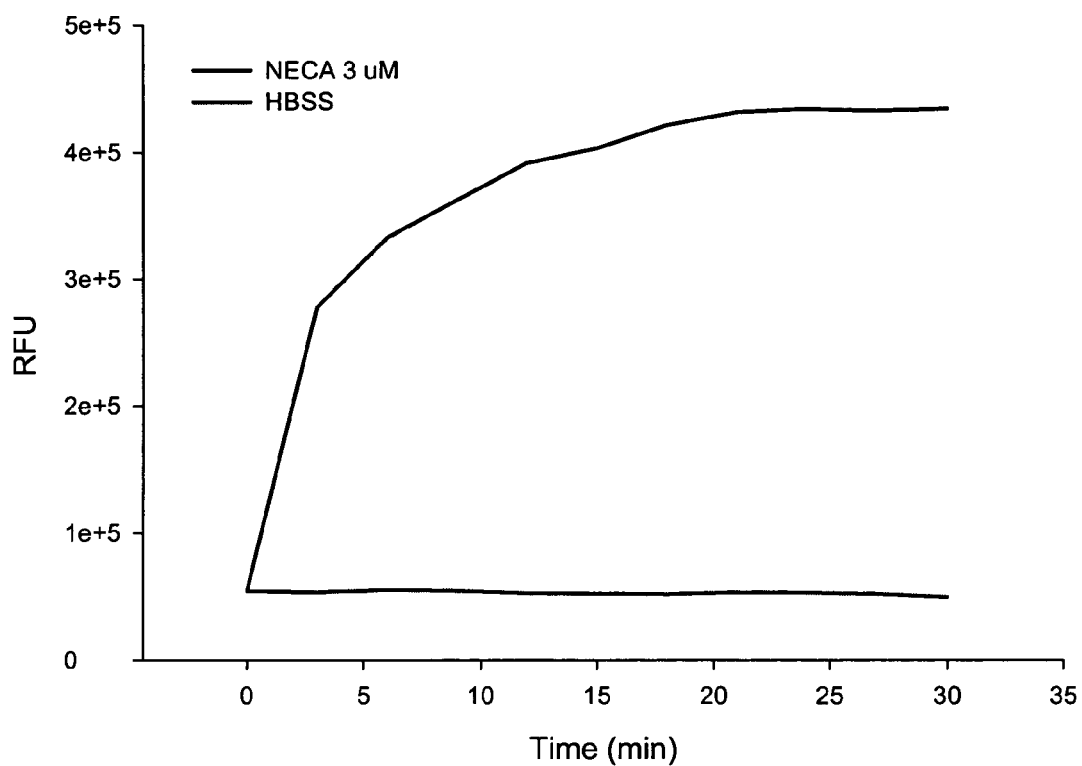
FIG. 4. Real-time record of the fluorescence change of Compound 4 in respond to GPCR agonist. Compound 4 solution is loaded to HEK293H-CNG cells in the presence of serum. The A2b receptor agonist, NECA (3 µM), or Hank's balance solution (control) is added to the cells. The fluorescence signal is continuously recorded at excitation 530 nm and emission 565 nm from time 0 min to time 30 min.
Figure 5:
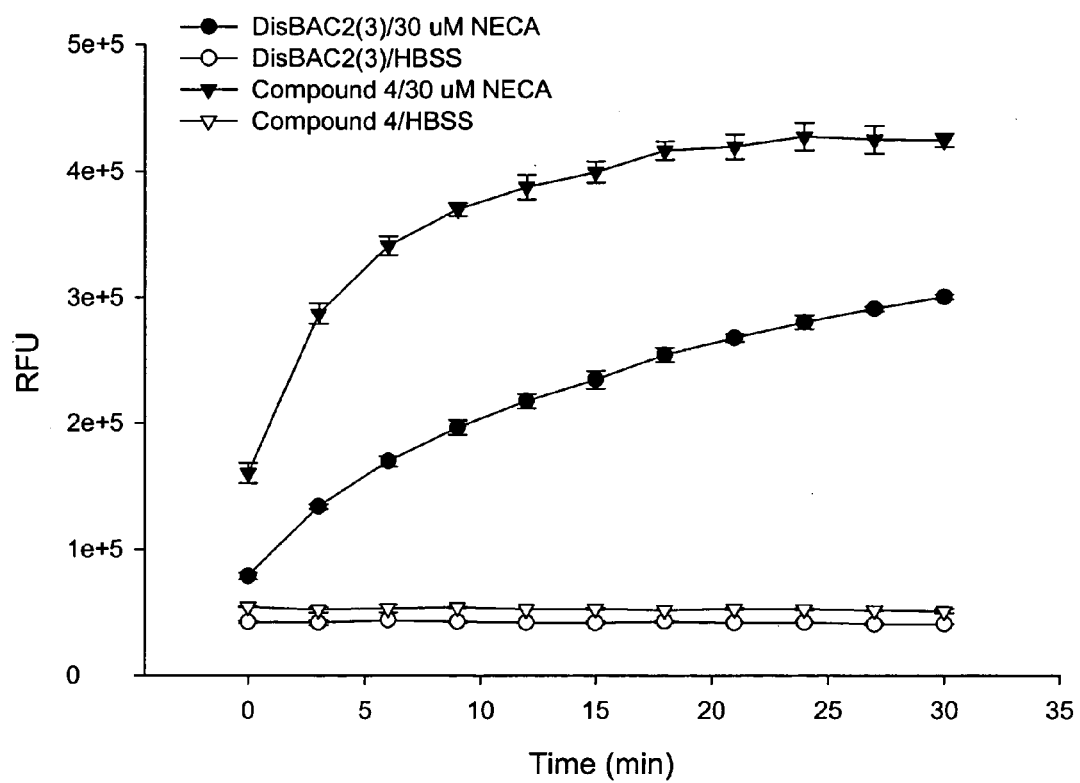
FIG. 5. Compare the fluorescent intensity of Compound 4 and $DisBAC_2(3)$. Compound 4 (15 µM) and $DisBAC_2(3)$ (15 µM) solutions are loaded to HEK293H-CNG cells in the presence of serum. The A2b receptor agonist, NECA, or Hank's balance solution (control) is added to the cells. The fluorescent signal is continuously recorded at excitation 530 nm and emission 565 nm from time 0 min to time 30 min (n=3 samples, mean±S.D.).

The HEK293 cell line that stably incorporates a CNG channel mutant gene is prepared, and then loaded with Compound 4 or 7 by incubating the cells for 2 hours at room temperature with the dye at 30 µM, in combination with a membrane-impermeable non-fluorescent dye to quench extracellular fluoescence (Sahlin S, Hed J, Rundquist I. 1983. "Differentiation between attached and ingested immune complexes by a fluorescence quenching cytofluorometric assay." J. Immunol. Methods 60:115-124). The CNG channels are activated by cyclic nucleotides (cGMP and cAMP), whereby the conducting cation currents are carried by mixed ions Na$^+$, K$^+$ and Ca$^{2+}$, and the changes in intracellular cyclic nucleotide concentration are coupled to membrane potential changes (Yao Y and Cao L. "Novel cell-based assays for G-protein-coupled receptor-mediated activities." United States Patent Application, 20030100059). [cAMP]$_i$ increase is detected by a membrane depolarization signal through CNG channels. The kinetic responses are recorded on a fluorescence plate reader, e.g., FLIPR or Flexstation (Molecular Devices Corp., Sunnyvale, Calif.). Activation of one endogenous G protein-coupled adenosine A2B receptor is detected by measuring membrane depolarization mediated through activation of CNG channels (see FIG. 4). Addition of NECA agonist affords the increase in fluorescence intensity of Compounds 4 or 7 by about 2-7 fold.

Example 12

The Cellular Distribution of Compound 4 Before and After Adding NECA

Figure 6:
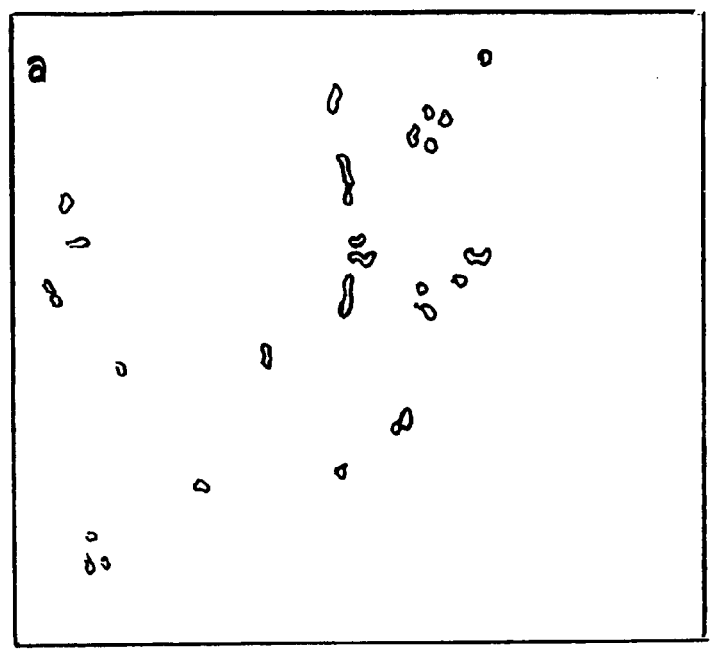
FIG. 6. The cellular distribution of Compound 4 before and after the addition of KCl. 3T3 is incubated with Compound 4 solution for 30 min. Then 120 mM KCl is added to depolarize the membrane potential. a. The fluorescence image before the addition of KCl. b. The fluorescence image at 30$^{th}$ sec after addition of 120 mM KCl. The filter set with exciter at 545/30 nm and emitter at 610/75 nm is used. Several fields had been examined and had the similar results.
Figure 6:

HEK293H-CNG is incubated with Compound 4 (30 µM) solution for 2 hr. a. The fluorescent image is taken before adding A2b receptor agonist, NECA. b. The image is acquired at the 30$^{th}$ min after adding 100 µM NECA. The filter set with exciter at 545/30 nm and emitter at 610/75 nm is used. Several fields are examined, and the similar results are observed (see FIG. 6).

Example 13

The Comparison of Serum Effect on the Baseline of Compound 4 and DiSBAC$_2$(3)

Figure 7:
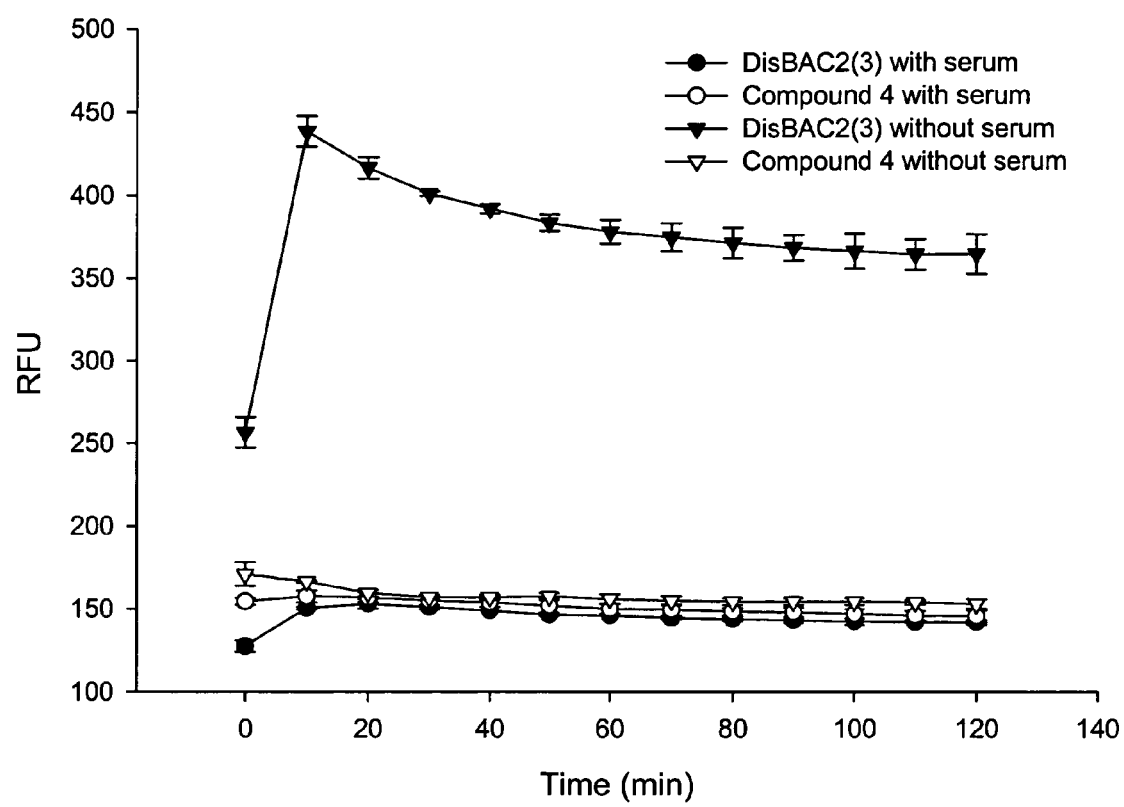
FIG. 7. The comparison of serum effect on the baseline of Compound 4 and DiSBAC$_2$(3). Compound 4 (30 μM) and DiSBAC$_2$ (3) (30 μM) solutions are loaded to HEK293H-CNG cells in the presence or absence of serum. The fluorescent signal is continuously recorded at excitation 530 nm and emission 565 nm from time 0 min to time 120 min (n=96 samples, mean±S.D.).
Figure 8A:
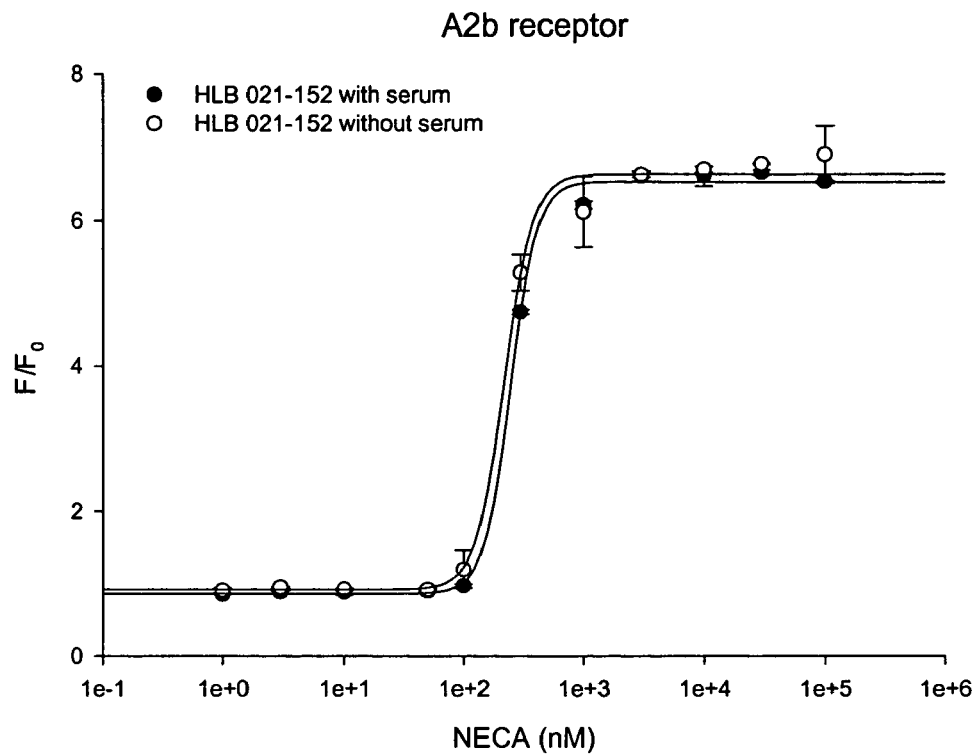
FIG. 8. The comparison of serum effect on the dynamic range of Compound 4 and DiSBAC$_2$(3) in CNG-GPCR cells. Several CNG cell lines containing different GPCRs are loaded with formulated Compound 4 or DiSBAC$_2$(3) with or without serum during the assay. The GPCRs are stimulated with their corresponding compounds. The fluorescence signals of Compound 4 and DiSBAC$_2$(3) are recorded before adding the stimulators ($F_0$) or 30 minutes after adding the stimulators (F). The $F/F_0$ is calculated and plotted versus the concentration of stimulators (n=2-4 samples, mean±S.D.).
a,b. The endogenous adenosine 2b receptor, stimulated with NECA.
c,d. The heterogenous prostaglandin E receptor 4, stimulated with prostaglandin E2.
e,f. The heterogenous dopamine receptor D1, stimulated with dopamine.
g,h. The heterogenous human parathyroid hormone receptor 2, stimulated with PTH$_{1-34}$.
Figure 8B:
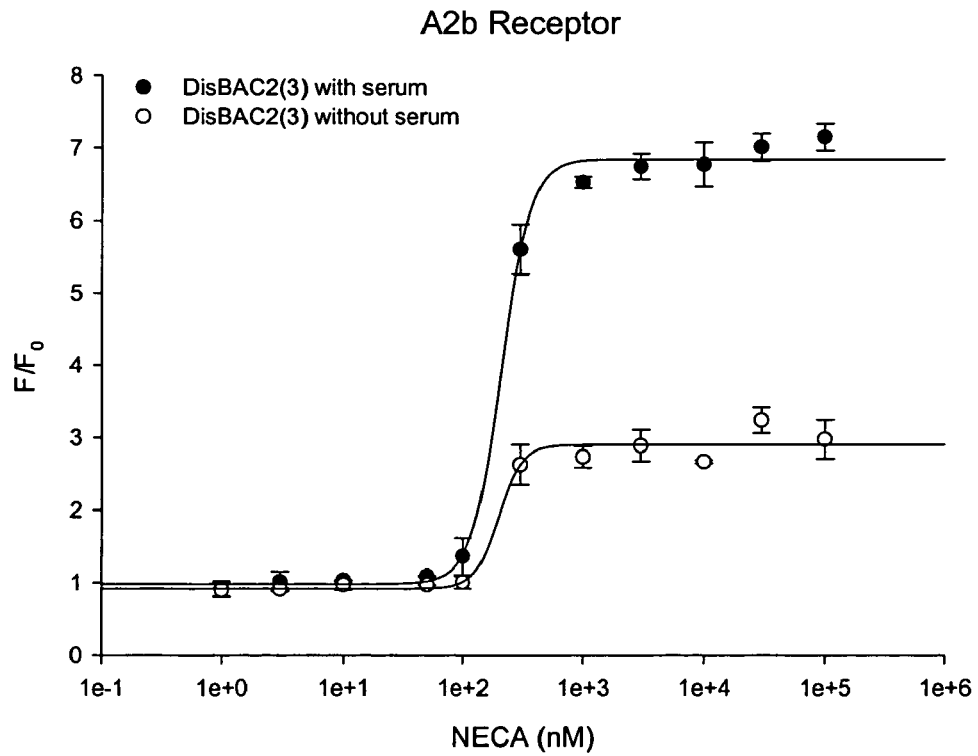
Figure 8C:
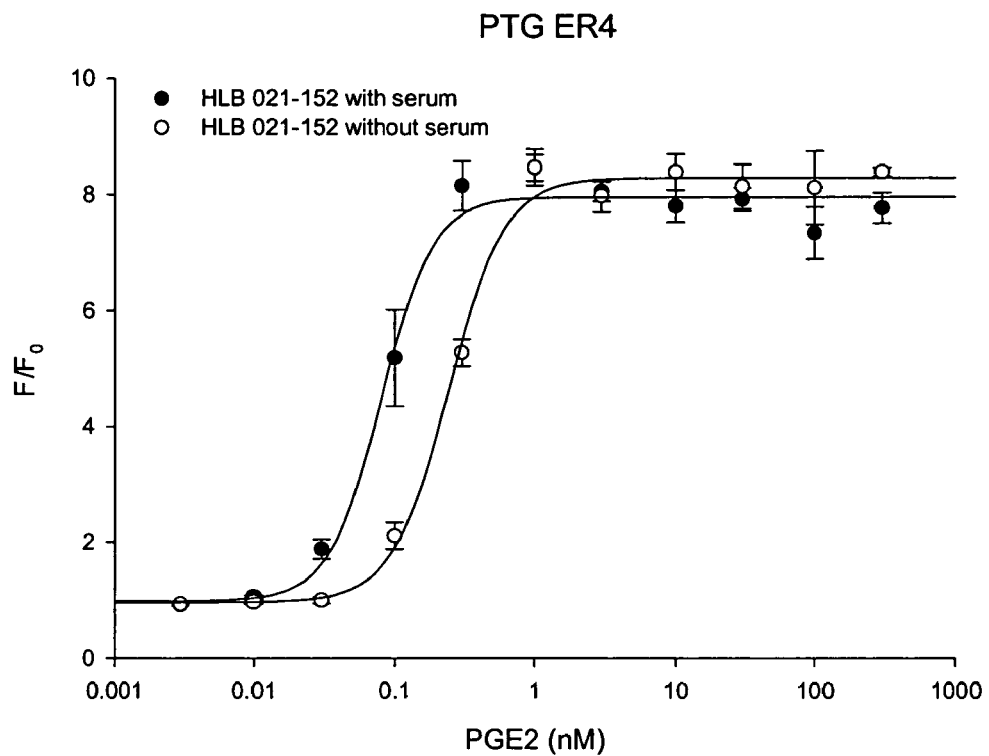
Figure 8D:
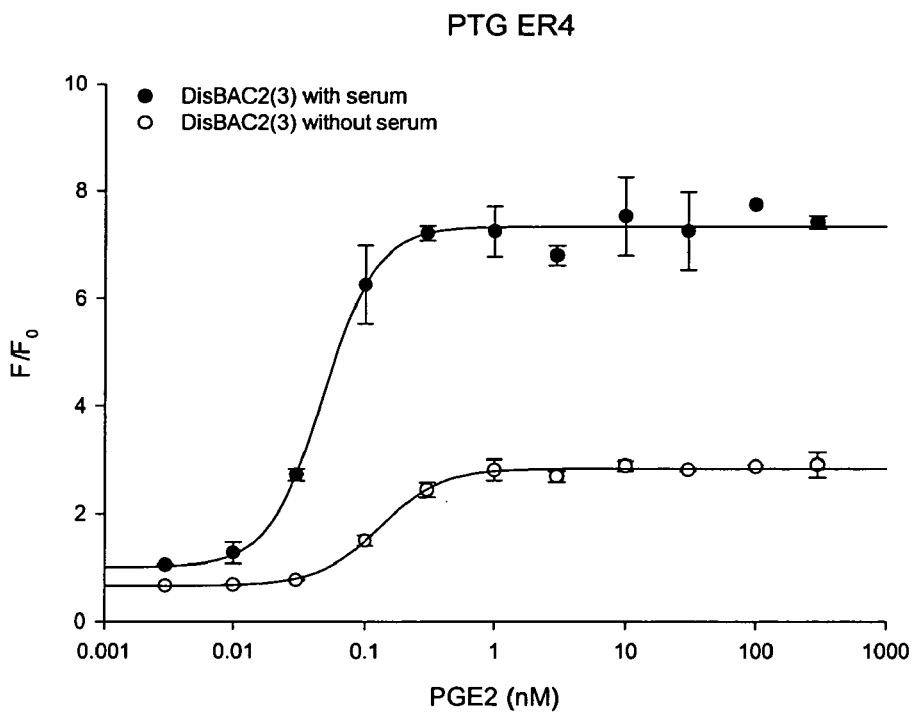
Figure 8E:
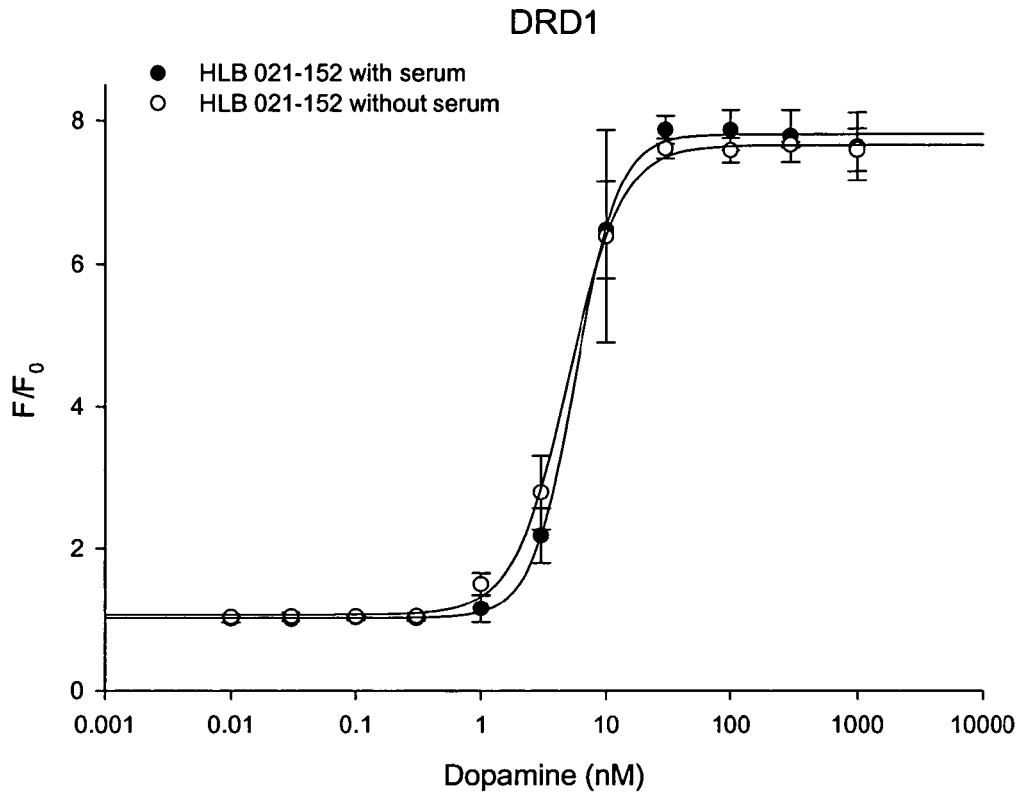
Figure 8F:
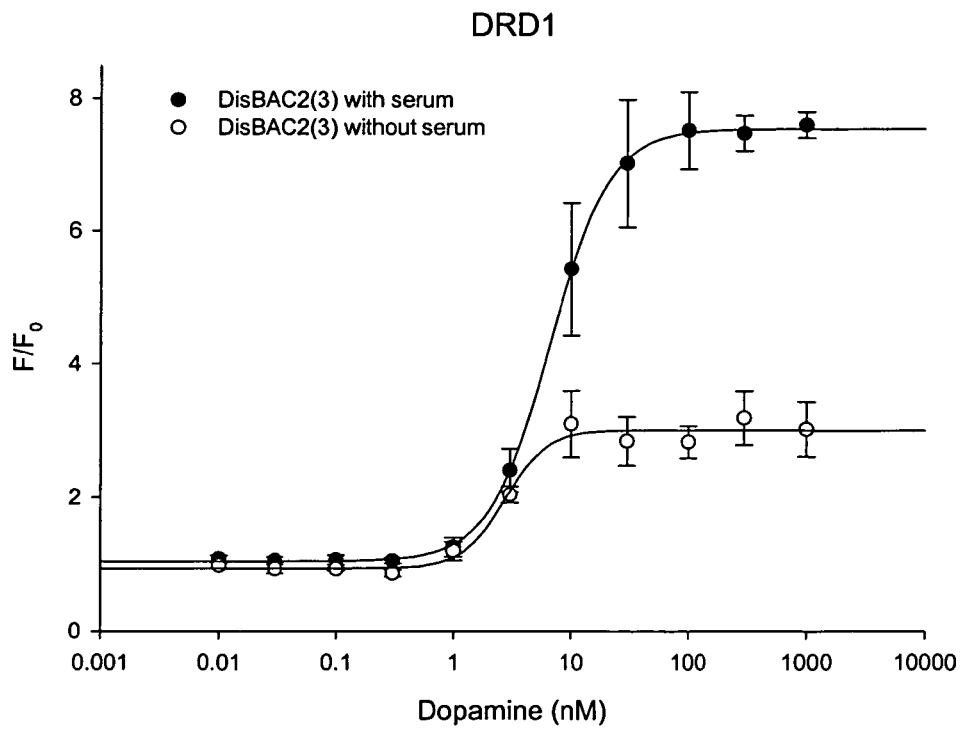
Figure 8G:
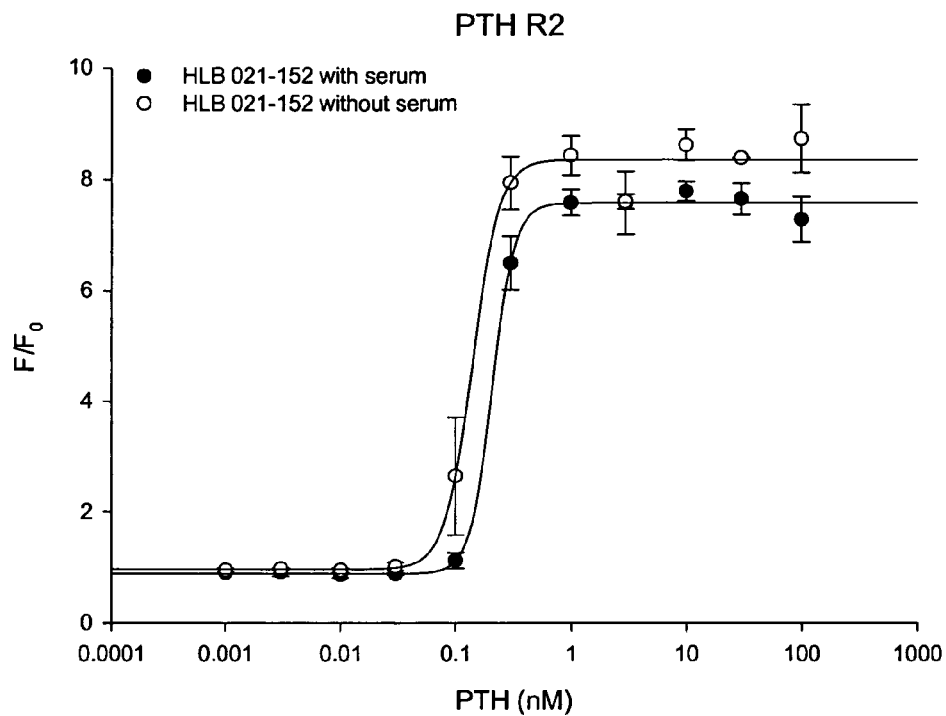
Figure 8H:
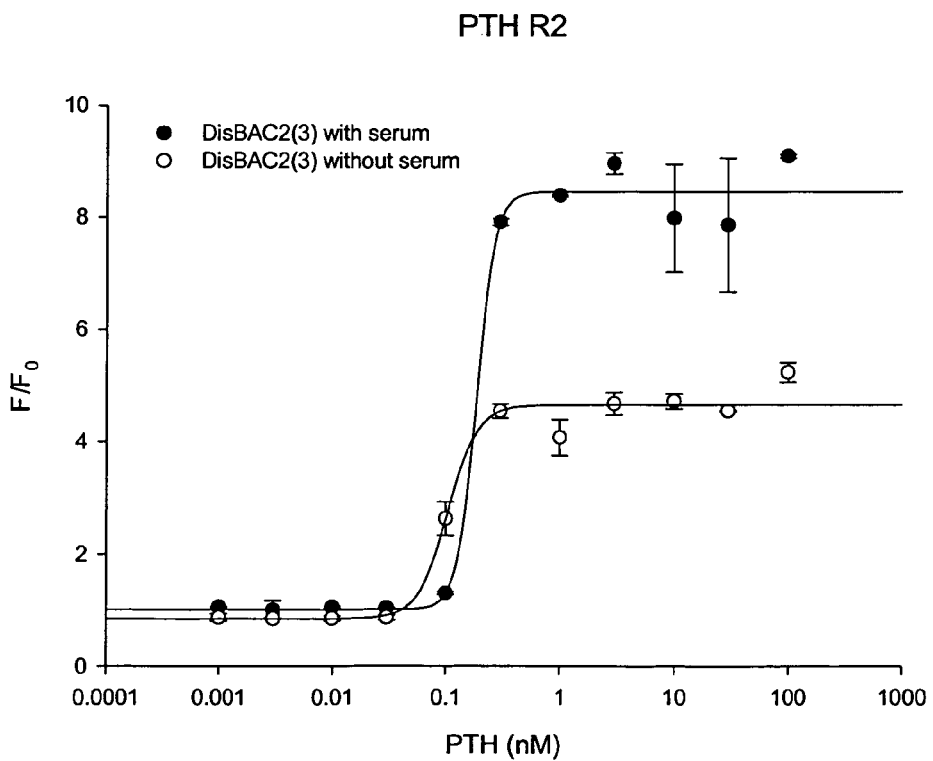

Compound 4 (30 µM) and DiSBAC$_2$(3) (30 µM) solutions are loaded to HEK293H-CNG cells in the presence or absence of serum. The fluorescence signal is continuously recorded at excitation 530 nm and emission 565 nm from time 0 min to time 120 min (n=96 samples, mean±S.D.). The results are shown in FIG. 7.

Example 14

The Comparison of Serum Effect on the Dynamic Range of Compound 4 and DiSBAC$_2$(3) in CNG-GPCR cells Several CNG cell lines containing different GPCRs are loaded with formulated Compound 4 or DiSBAC$_2$(3) with or without serum during the assay. The GPCRs are stimulated with their corresponding compounds. The fluorescence signals of Compound 4 and DiSBAC$_2$(3) are recorded before adding the stimulators ($F_0$) or 30 minutes after adding the stimulators (F). The F/F$_0$ is calculated and plotted versus the concentration of stimulators (n=2-4 samples, mean±S.D.). The results are shown in FIG. 8.

Example 15

Figure 9:
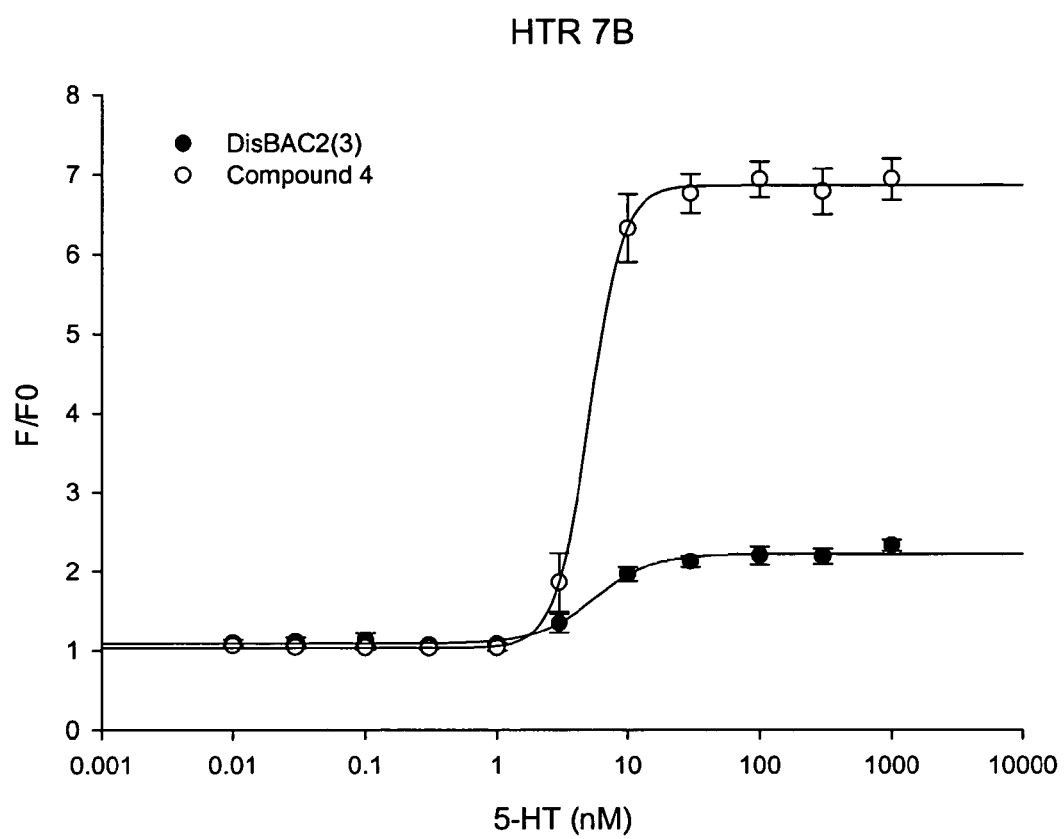
FIG. 9. The comparison of the dynamic range of Compound 4 and DiSBAC$_2$(3) for measuring the dose response of 5-hydroxytryptamine (5-HT) in HTR7B-CNG cell line.

The Comparison of the Dynamic Range of Compound 4 and DiSBAC$_2$(3) for Measuring the Dose Response of 5-hydroxytryptamine (5-HT) in HTR7B-CNG Cell Line The HTR7B-CNG cells cultured in serum-free medium is loaded with Compound 4 (30 μM) or DiSBAC$_2$(3) (30 μM) solution for 2 hr. The serial diluted 5-HT is added into the cells to stimulate human 5-hydroxytryptamine receptor 7B. The fluorescence signals of Compound 4 and DiSBAC$_2$(3) are recorded before adding 5-HT ($F_0$) or 30 minutes after adding 5-HT (F). The F/F$_0$ is calculated and plotted versus the concentration of 5-HT (n=4, mean±SD). The results are shown in FIG. 9.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A test kit for measuring membrane potential changes comprising the following compound as a reagent:

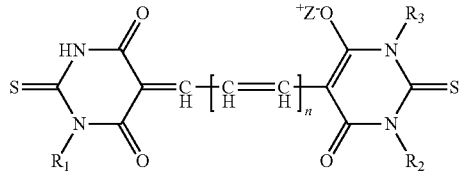

wherein $R_1$, $R_2$, and $R_3$ are methyl; n is the integer 1; Z is H, Na, K, ammonium or other biologically acceptable salt.

2. The test kit according to claim 1, further comprising a solubilizing agent.

3. The test kit according to claim 2 further comprising a second fluorescent agent.

4. The test kit according to claim 2 further comprising a second non-fluorescent colored reagent.

* * * * *